(12) United States Patent
Sawamoto et al.

(10) Patent No.: US 11,667,730 B2
(45) Date of Patent: Jun. 6, 2023

(54) OXIME ESTER COMPOUND AND PHOTOPOLYMERIZATION INITIATOR CONTAINING THE SAME

(71) Applicant: ADEKA CORPORATION, Tokyo (JP)

(72) Inventors: Daisuke Sawamoto, Tokyo (JP); Koichi Kimijima, Tokyo (JP); Kiyoshi Murata, Tokyo (JP); Yasunori Kozaki, Tokyo (JP); Takeo Oishi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/629,773

(22) Filed: Jun. 22, 2017

(65) Prior Publication Data

US 2017/0283520 A1 Oct. 5, 2017

Related U.S. Application Data

(62) Division of application No. 12/447,139, filed as application No. PCT/JP2007/074646 on Dec. 21, 2007, now abandoned.

(30) Foreign Application Priority Data

Dec. 27, 2006 (JP) .............. JP2006-351996
Aug. 28, 2007 (JP) .............. JP2007-221710

(51) Int. Cl.
| | | |
|---|---|---|
| C08F 2/50 | (2006.01) | |
| C07D 209/88 | (2006.01) | |
| G03F 7/004 | (2006.01) | |
| G03F 7/031 | (2006.01) | |

(52) U.S. Cl.
CPC .............. *C08F 2/50* (2013.01); *C07D 209/88* (2013.01); *G03F 7/0045* (2013.01); *G03F 7/031* (2013.01)

(58) Field of Classification Search
CPC ......... C08F 2/50; C07D 209/88; G03F 7/031; G03F 7/0045
See application file for complete search history.

(56) References Cited

U.S. PATENT DOCUMENTS

| | | |
|---|---|---|
| 6,949,678 B2 | 9/2005 | Kunimoto et al. |
| 7,189,489 B2 | 3/2007 | Kunimoto et al. |
| 2001/0012596 A1 | 8/2001 | Kunimoto et al. |
| 2004/0170924 A1 | 9/2004 | Kunimoto et al. |
| 2005/0191567 A1 | 9/2005 | Kunimoto et al. |

FOREIGN PATENT DOCUMENTS

| | | | |
|---|---|---|---|
| JP | 2001-233842 | 8/2001 | |
| JP | 2001-302871 | 10/2001 | |
| JP | 2004-534797 | 11/2004 | |
| JP | 2005-025169 | 1/2005 | |
| JP | 2005-128483 | 5/2005 | |
| JP | 2005-242279 | 9/2005 | |
| JP | 2005-242280 | 9/2005 | |
| JP | 3754065 | 12/2005 | |
| JP | 2006-016545 | 1/2006 | |
| WO | 02/10903 | 12/2002 | |
| WO | 2006/018973 | 2/2006 | |
| WO | 2007/062963 | 6/2007 | |
| WO | WO 2007-071497 | * 6/2007 | ............... C08F 2/50 |
| WO | 2008/078686 | 7/2008 | |

OTHER PUBLICATIONS

Kamimura et al., machine English translation of JP 2006-016545, pub date. Jan. 19, 2006 (2 documents).
Supplementary European Search Report dated Nov. 24, 2010 in corresponding European Application No. EP 07 85 1050.

\* cited by examiner

*Primary Examiner* — Jessica M Roswell
(74) *Attorney, Agent, or Firm* — Nixon & Vanderhye

(57) ABSTRACT

An oxime ester compound represented by general formula (I):

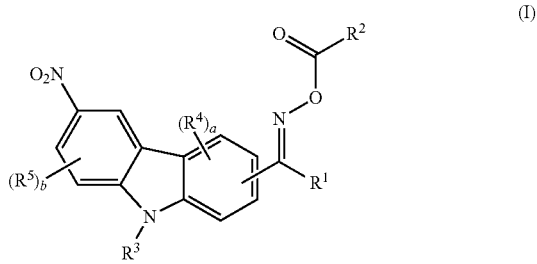

wherein $R^1$, $R^2$, and $R^3$ each independently represent $R^{11}$, $OR^{11}$, $COR^{11}$, $SR^{11}$, $CONR^{12}R^{13}$, or CN; $R^{11}$, $R^{12}$, and $R^{13}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, $R^4$ and $R^5$ each independently represent $R^{11}$, $OR^{11}$, $SR^{11}$, $COR^{11}$, $CONR^{12}R^{13}$, $NR^{12}COR^{11}$, $OCOR^{11}$, $COOR^{11}$, $SCOR^{11}$, $OCSR^{11}$, $COSR^{11}$, $CSOR^{11}$, CN, a halogen atom, or a hydroxyl group; and a and b each independently represent 0 to 3.

2 Claims, No Drawings

OXIME ESTER COMPOUND AND PHOTOPOLYMERIZATION INITIATOR CONTAINING THE SAME

TECHNICAL FIELD

This invention relates to a novel oxime ester compound useful as a photopolymerization initiator in a photosensitive composition, a photopolymerization initiator containing the compound as an active ingredient, and a photosensitive composition containing a polymerizable compound having an ethylenically unsaturated bond and the photopolymerization initiator.

BACKGROUND ART

A photosensitive composition contains a polymerizable compound having an ethylenically unsaturated bond and a photopolymerization initiator. A photosensitive composition polymerizes to cure on being irradiated with light of 405 nm or 365 nm and is used in photo-curing inks, photosensitive printing plate precursors, and various photoresists.

Patent documents 1 to 8 listed below propose using an O-acyl oxime compound having a carbazolyl structure as a photopolymerization initiator of a photosensitive composition. However, the known O-acyl oxime compounds are not sufficiently satisfactory particularly in sensitivity.

Patent document 1: JP 2001-302871A
Patent document 2: JP 2004-534797A
Patent document 3: JP 2005-25169A
Patent document 4: JP 2005-128483A
Patent document 5: JP 2005-242279A
Patent document 6: JP 2005-242280A
Patent document 7: JP 2006-16545A
Patent document 8: Japanese Patent 3754065

DISCLOSURE OF THE INVENTION

Problem to be Solved by the Invention

The problem to be solved is that there has been no photopolymerization initiator having satisfactory sensitivity.

Accordingly, an object of the invention is to provide a highly sensitive photopolymerization initiator that efficiently absorbs light of long wavelength, e.g., 405 nm or 365 nm, to be activated.

Means for Solving the Problem

The above object is accomplished by the provision of an oxime ester compound represented by general formula (I) below and a photopolymerization initiator containing the oxime ester compound as an active ingredient.

[Formula 1]

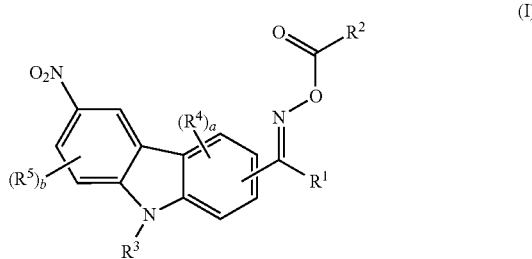

(I)

wherein $R^1$, $R^2$, and $R^3$ each independently represent $R^{11}$, $OR^{11}$, $COR^{11}$, $SR^{11}$, $CONR^{12}R^{13}$, or CN; $R^{11}$, $R^{12}$, and $R^{13}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms, in which the alkyl group, aryl group, arylalkyl group, and heterocyclic group may have their hydrogen atom substituted with $OR^{21}$, $COR^{21}$, $SR^{21}$, $NR^{22}R^{23}$, $CONR^{22}R^{23}$, —$NR^{22}$—$OR^{23}$, —$NCOR^{22}$—$OCOR^{23}$, —$C(=N-OR^{21})$—$R^{22}$, —$C(=N-OCOR^{21})$—$R^{22}$, CN, a halogen atom, —$CR^{21}=CR^{22}R^{23}$, —CO—$CR^{21}=CR^{22}R^{23}$, a carboxyl group, or an epoxy group; $R^{21}$, $R^{22}$, and $R^{23}$ each independently represent a hydrogen atom, an alkyl group having 1 to 20 carbon atoms, an aryl group having 6 to 30 carbon atoms, an arylalkyl group having 7 to 30 carbon atoms, or a heterocyclic group having 2 to 20 carbon atoms; the methylene units of the alkylene moiety of the substituents represented by $R^{11}$, $R^{12}$, $R^{13}$, $R^{21}$, $R^{22}$, and $R^{23}$ may be interrupted by an unsaturated linkage, an ether linkage, a thioether linkage, an ester linkage, a thioester linkage, an amide linkage, or a urethane linkage at 1 to 5 sites thereof; the alkyl moiety of the substituents represented by $R^{11}$, $R^{12}$, $R^{13}$, $R^{21}$, $R^{22}$, and $R^{23}$ may be branched or cyclic; an alkyl terminal of the substituents represented by $R^{11}$, $R^{12}$, $R^{13}$, $R^{21}$, $R^{22}$, and $R^{23}$ may have an unsaturated bond; $R^{12}$ and $R^{13}$, and $R^{22}$ and $R^{23}$ may be connected to each other form a ring; $R^3$ may be taken together with a neighboring benzene ring; $R^4$ and $R^5$ each independently represent $R^{11}$, $OR^{11}$, $SR^{11}$, $COR^{11}$, $CONR^{12}R^{13}$, $NR^{12}COR^{11}$, $OCOR^{11}$, $COOR^{11}$, $SCOR^{11}$, $OCSR^{11}$, $COSR^{11}$, $CSOR^{11}$, CN, a halogen atom, or a hydroxyl group; and a and b each independently represent 0 to 3.

The invention also provides a photosensitive composition containing the photopolymerization initiator and a polymerizable compound having an ethylenically unsaturated bond.

The invention also provides an alkali-developable photosensitive resin composition containing the photopolymerization initiator and an alkali-developable compound having an ethylenically unsaturated bond.

The invention also provides a colored alkali-developable photosensitive resin composition comprising the alkali-developable photosensitive resin composition and a colorant.

BEST MODE FOR CARRYING OUT THE INVENTION

The oxime ester compound of the invention and a photopolymerization initiator containing the compound as an active ingredient will be described in detail.

The oxime ester compound according to the invention embraces geometric isomers based on the double bond of oxime. Either of the isomers is useful. The general formula (I) and the formulae of specific examples of the compounds given later each represent either one of the isomers or a mixture of the isomers, not being limited to the isomeric structure shown.

In general formula (I), examples of the alkyl group as represented by $R^{11}$, $R^{12}$, $R^{13}$, $R^{21}$, $R^{22}$, and $R^{23}$ include methyl, ethyl, propyl, isopropyl, butyl, isobutyl, sec-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl, eicosyl, cyclopentyl, cyclohexyl, cyclohexylmethyl, vinyl, allyl, butenyl, ethynyl, propynyl, methoxyethyl, ethoxyethyl, propoxyethyl, pentyloxyethyl, octyloxyethyl, methoxyethoxyethyl, ethoxyethoxyethyl, propoxyethoxyethyl, methoxypropyl, and 2-methoxy-1-methylethyl. Examples of the aryl group as represented by $R^{11}$, $R^{12}$, $R^{13}$, $R^{21}$, $R^{22}$, and $R^{23}$ include phenyl, tolyl, xylyl, ethylphenyl, chlorophenyl, naphthyl, anthryl, phenanthryl; and phenyl, biphenylyl, naphthyl or anthryl substituted with at least one of the above recited alkyl groups. Examples of the arylalkyl group as represented by $R^{11}$, $R^{12}$, $R^{13}$, $R^{21}$, $R^{22}$, and $R^{23}$ include benzyl, chlorobenzoyl, α-methylbenzyl, α,α-dimethylbenzyl, phenylethyl, and phenylethenyl. The heterocyclic group as represented by $R^{11}$, $R^{12}$, $R^{13}$, $R^{21}$, $R^{22}$, and $R^{23}$ is preferably a 5- to 7-membered heterocyclic group, including pyridyl, pyrimidyl, furyl, thienyl, tetrahydrofuryl, dioxolanyl, benzoxazol-2-yl, tetrahydropyranyl, pyrrolidyl, imidazolidyl, pyrazolidyl, thiazolidyl, isothiazolidyl, oxazolidyl, isooxazolidyl, piperidyl, piperazyl, and morpholinyl. Examples of the ring formed by connecting $R^{12}$ and $R^{13}$, the ring formed by connecting $R^{22}$ and $R^{23}$, and the ring formed by connecting $R^3$ and a neighboring benzene ring include 5- to 7-membered rings, such as cyclopentane, cyclohexane, cyclopentene, benzene, piperidine, morpholine, lactone, and lactam rings. Examples of the halogen atom as a substituent of $R^{11}$, $R^{12}$, $R^{13}$, $R^{21}$, $R^{22}$, and $R^{23}$ and the halogen atom represented by $R^4$ and $R^5$ include fluorine, chlorine, bromine, and iodine.

The methylene units of the alkylene moiety of the above described substituents may be interrupted by an unsaturated linkage, an ether linkage, a thioether linkage, an ester linkage, a thioester linkage, an amido linkage, or a urethane linkage at 1 to 5 sites. The interrupting linking groups may be the same or different. Two or more interrupting linking groups may be continued to each other, if possible. The alkyl moiety of the above described substituents may be branched or cyclic, and the alkyl terminal of the substituents may have an unsaturated bond.

Preferred of the oxime ester compounds of general formula (I) according to the invention are those in which $R^1$ is an alkyl group having 11 to 20 carbon atoms, an aryl group having 6 to 30 carbon atoms, an arylalkyl group having 7 to 30 carbon atoms, a heterocyclic group having 2 to 20 carbon atoms, $OR^{11}$, $COR^{11}$, $SR^{11}$, $CONR^{12}R^{13}$, or CN and those in which $R^3$ is an alkyl group having 1 to 12 carbon atoms and interrupted by an ether linkage or an ester linkage at 1 to 5 sites, an alkyl group having 13 to 20 carbon atoms, $OR^{11}$, $COR^{11}$, $SR^{11}$, $CONR^{12}R^{13}$, or CN. Particularly preferred are those in which $R^1$ is an alkyl group having 11 to 20 carbon atoms or an aryl group having 6 to 30 carbon atoms, or $R^3$ is a branched alkyl group having 8 or more carbon atoms the methylene units of which may be interrupted by an ether linkage or an ester linkage at 1 to 5 sites; those in which $R^3$ is an alkyl group having 13 or more carbon atoms the methylene units of which may be interrupted by an ether linkage or an ester linkage at 1 to 5 sites; those in which $R^3$ is an alkyl group interrupted by an ether linkage at 1 to 5 sites; and those in which $R^3$ is an alkyl group interrupted by an ester linkage at 1 to 5 sites. These preferred compounds are easy to synthesize and show high sensitivity.

When used as a photopolymerization initiator, they dissolve in propylene glycol-1-monomethyl ether-2-acetate or cyclohexanone as a solvent to a concentration of 1% by mass or higher, to satisfy the requirement as a photopolymerization initiator. The solubility measurement is preferably made at 20° to 30° C.

The oxime ester compound of the invention may be dimerized at $R^1$ or $R^2$ to provide a compound represented by formulae shown below:

[Formula 2]

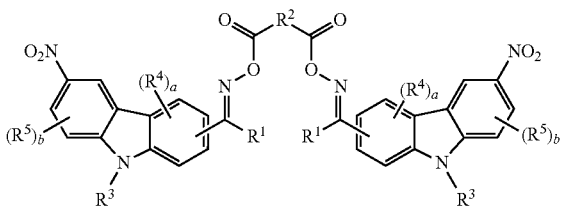

[Formula 3]

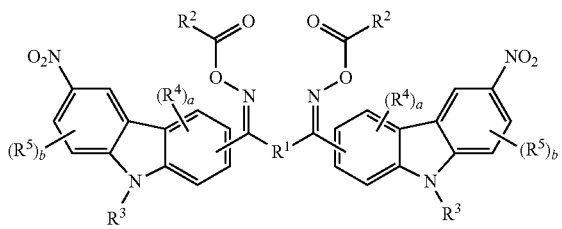

Examples of the preferred oxime ester compounds of general formula (I) include, but are not limited to, compound Nos. 1 through 71 below.

[Formula 4]

Compound No. 1

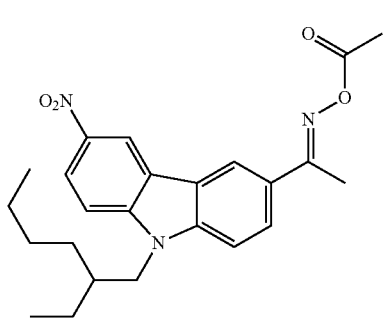

Compound No. 2

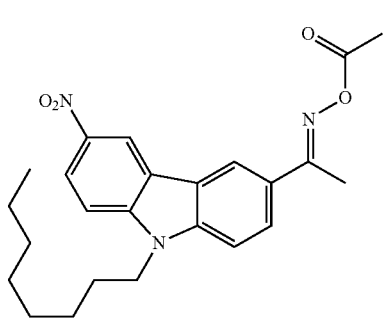

-continued
Compound No. 3
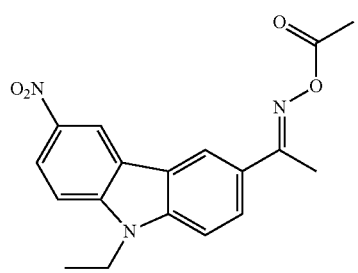
Compound No. 4
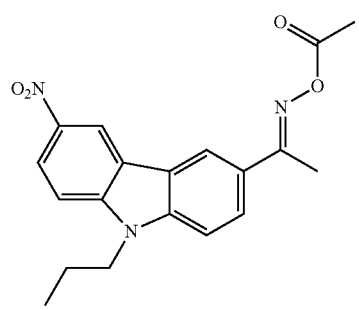
Compound No. 5
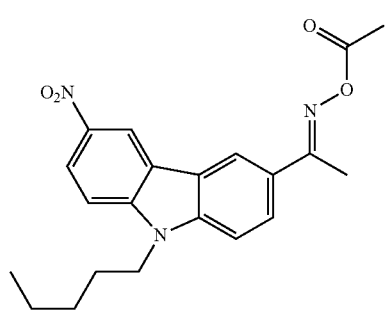
Compound No. 6
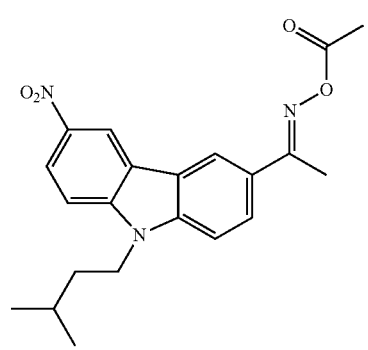
Compound No. 7
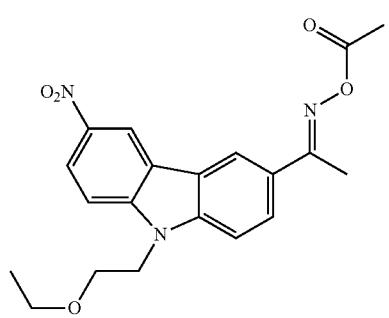
Compound No. 8
Compound No. 9
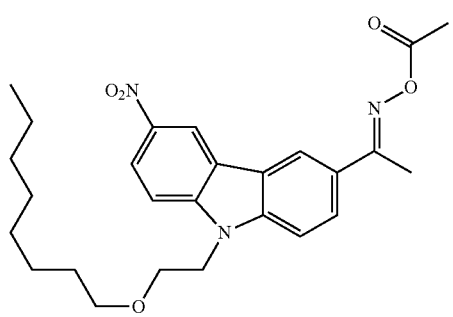
Compound No. 10
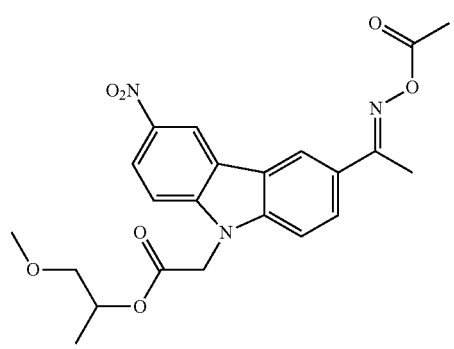

-continued
Compound No. 11
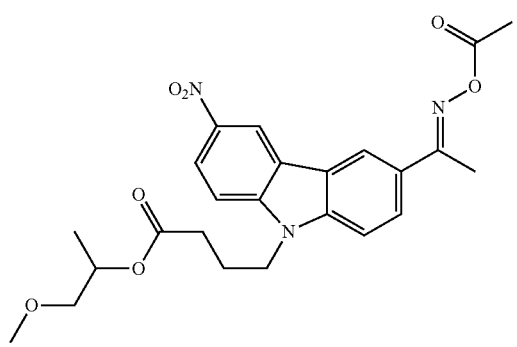
Compound No. 12
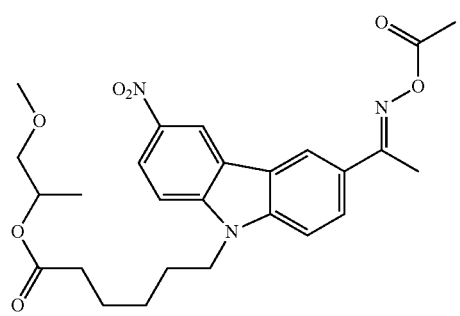
Compound No. 13
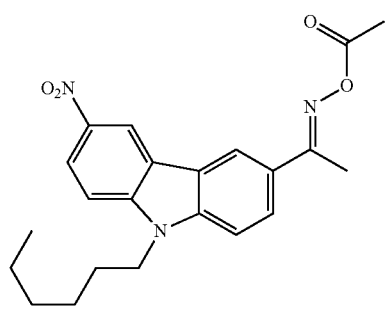
Compound No. 14
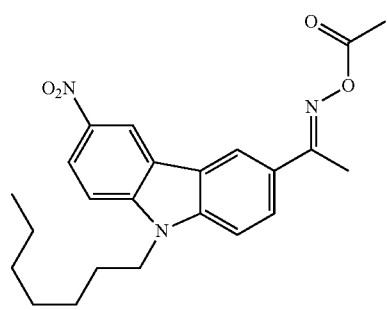
Compound No. 15
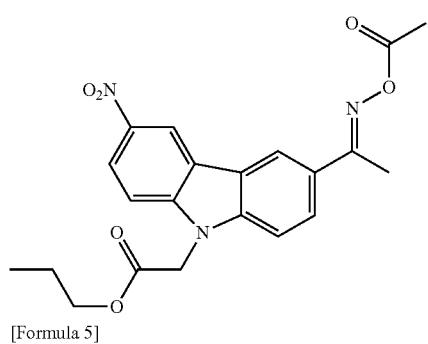
[Formula 5]
Compound No. 16
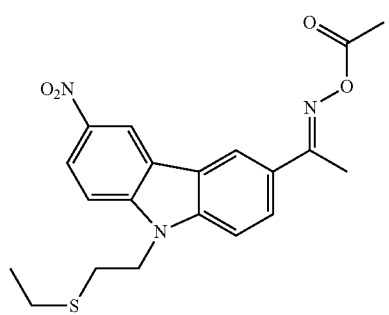
Compound No. 17
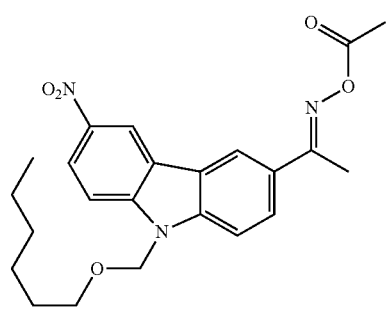

-continued
Compound No. 18
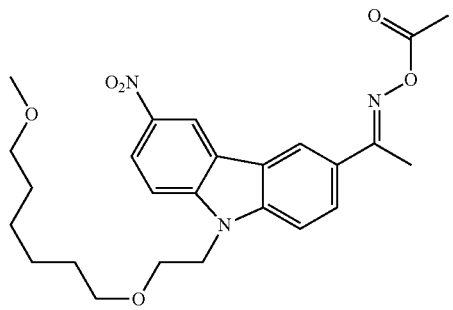
Compound No. 19
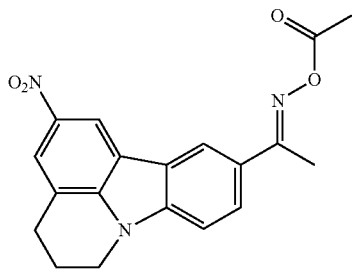
Compound No. 20
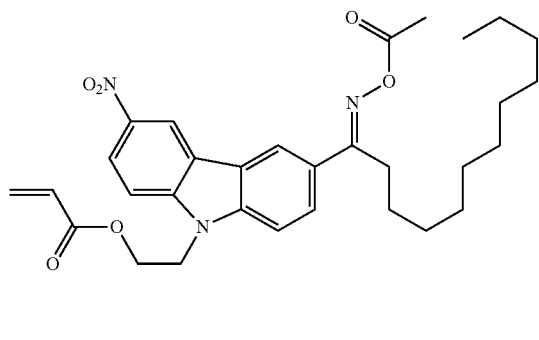
Compound No. 21
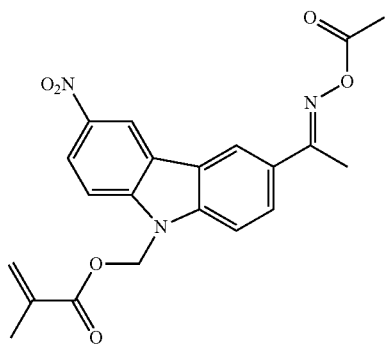
Compound No. 22
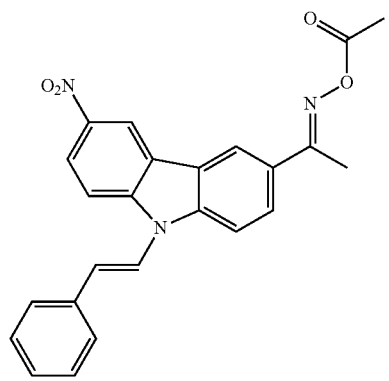
Compound No. 23
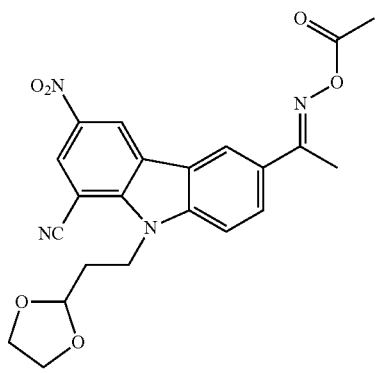
Compound No. 24
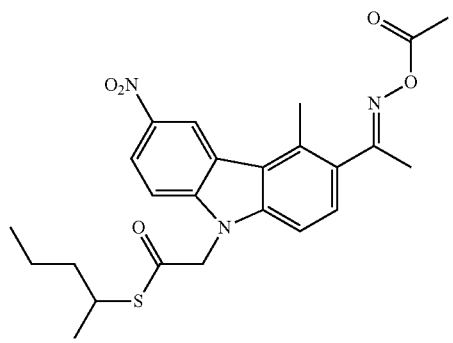
Compound No. 25
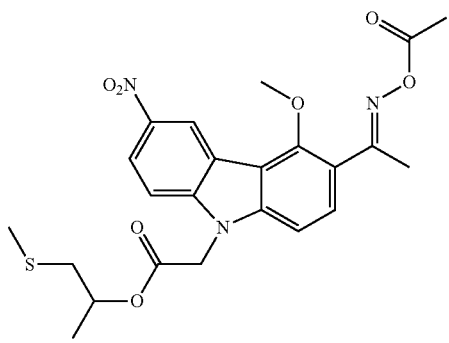

-continued
Compound No. 26
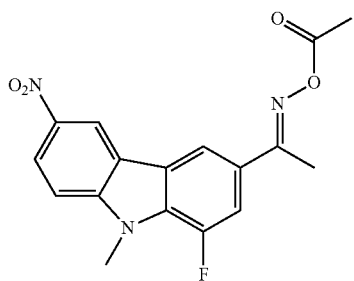
Compound No. 27
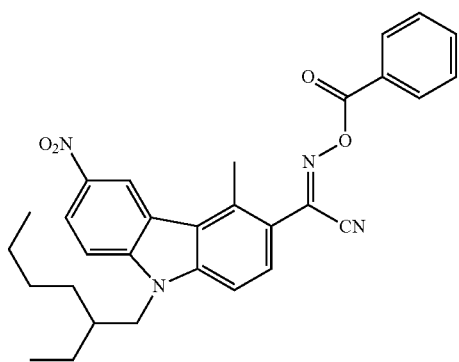
Compound No. 28
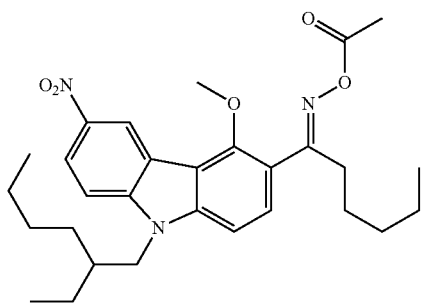
Compound No. 29
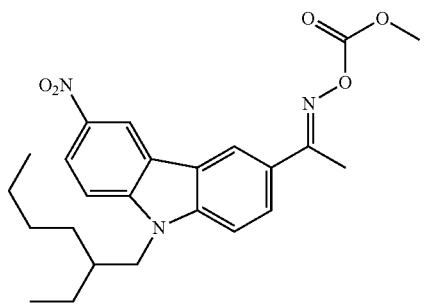
Compound No. 30
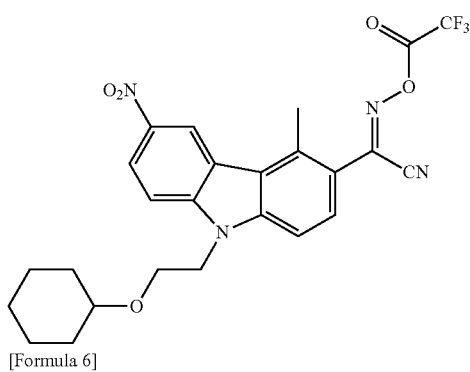
[Formula 6]
Compound No. 31
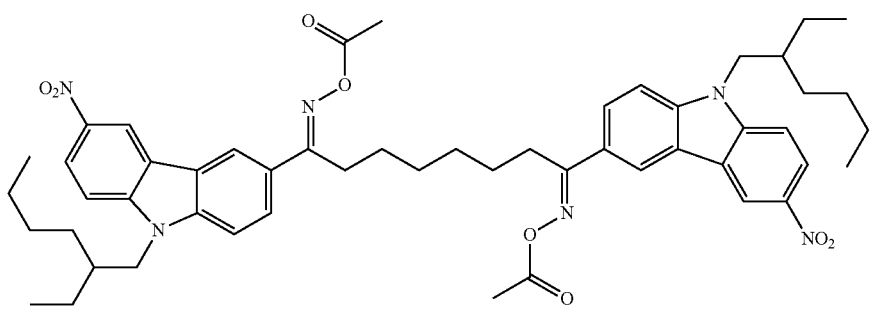

-continued
Compound No. 32
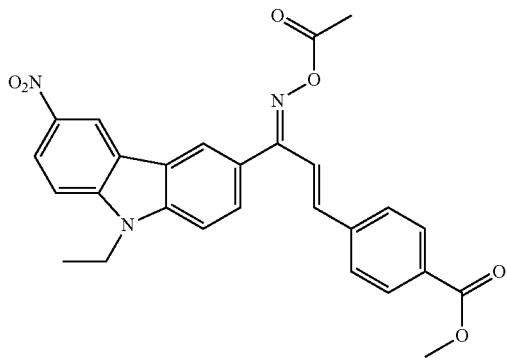
Compound No. 33
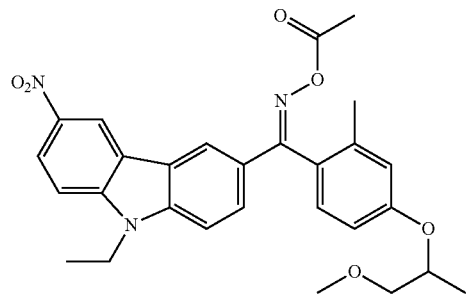
Compound No. 34
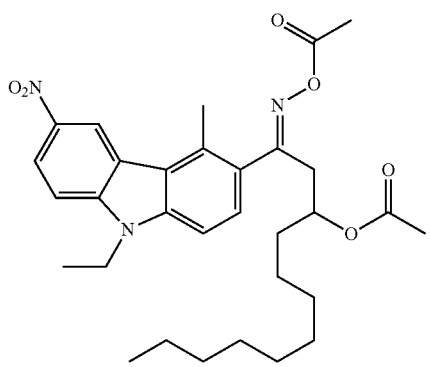
Compound No. 35
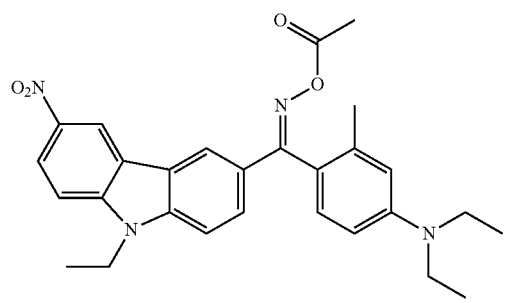
Compound No. 36
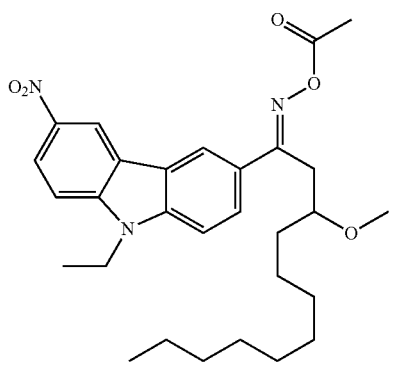
Compound No. 37
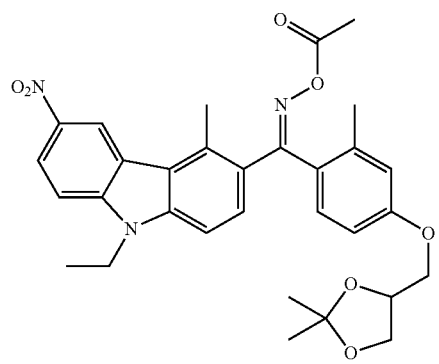
Compound No. 38
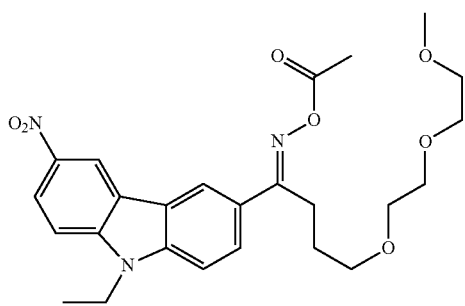
Compound No. 39
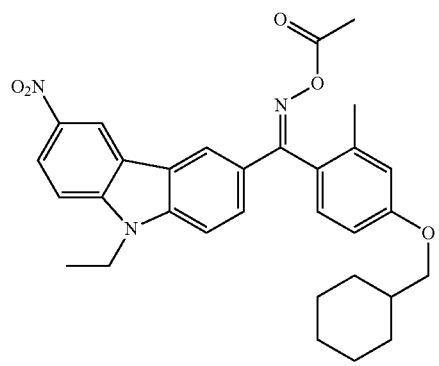

-continued
Compound No. 40
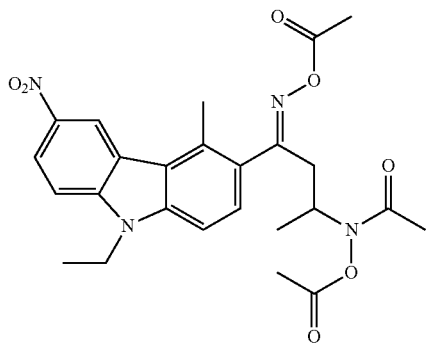
Compound No. 41
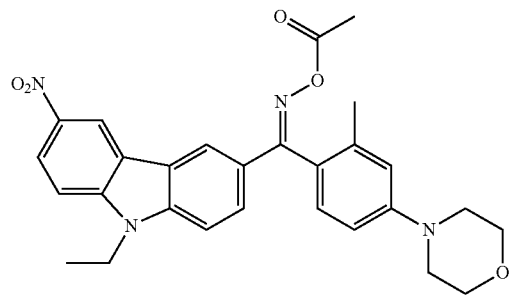
Compound No. 42
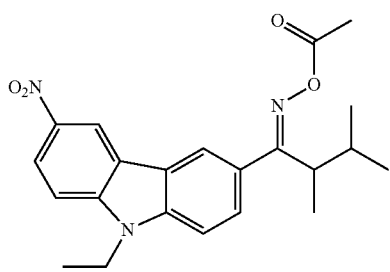
Compound No. 43
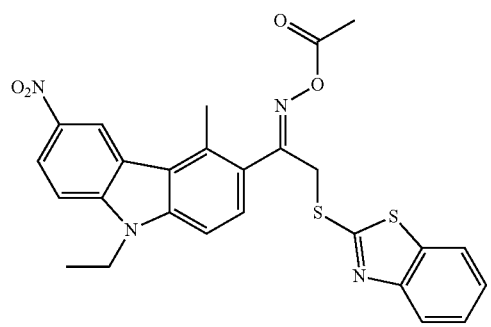
[Formula 7]
Compound No. 44
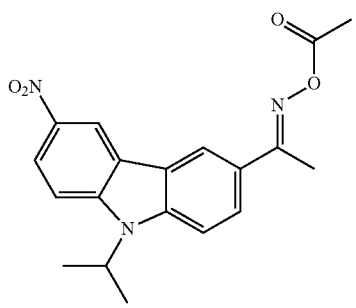
Compound No. 45
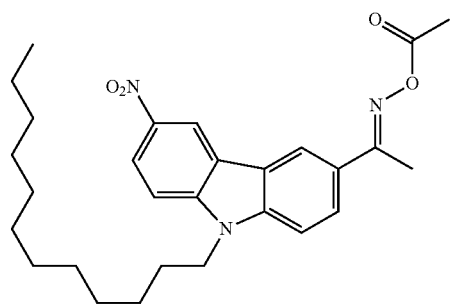
Compound No. 46
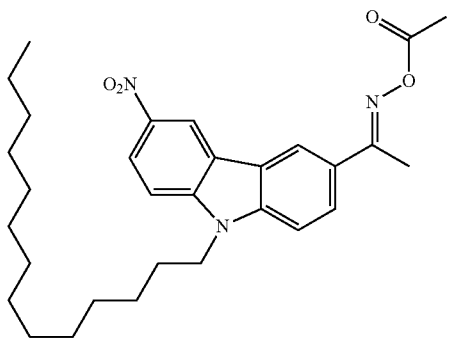
Compound No. 47
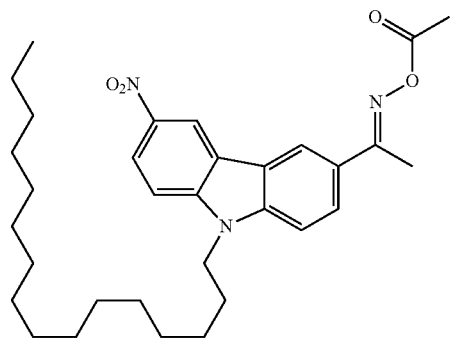

-continued
Compound No. 48
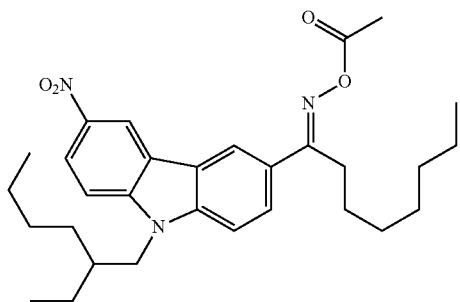
Compound No. 49
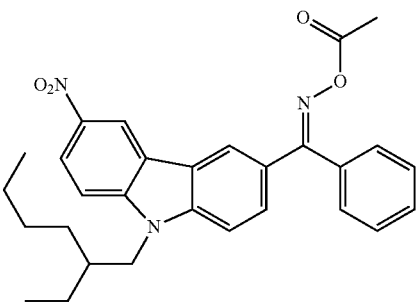
Compound No. 50
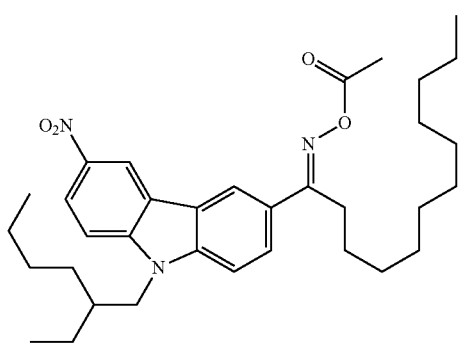
Compound No. 51
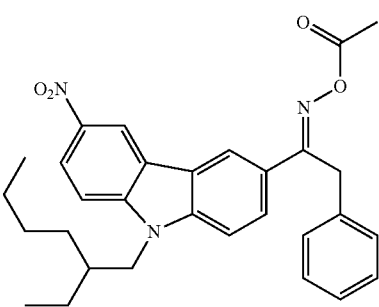
Compound No. 52
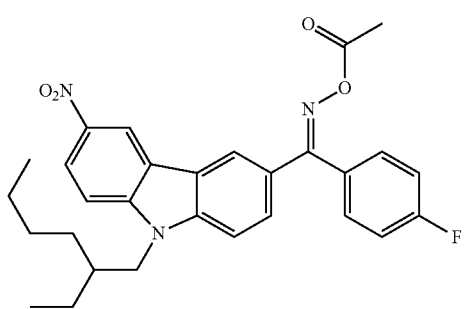
Compound No. 53
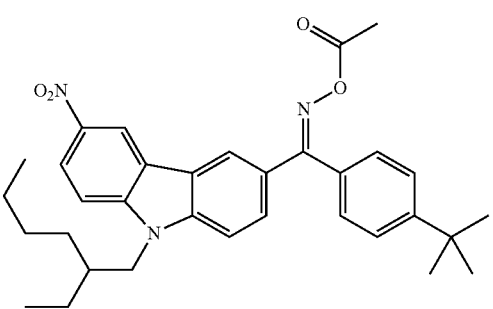
Compound No. 54
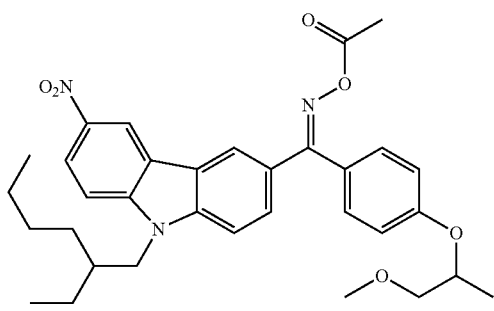
Compound No. 55
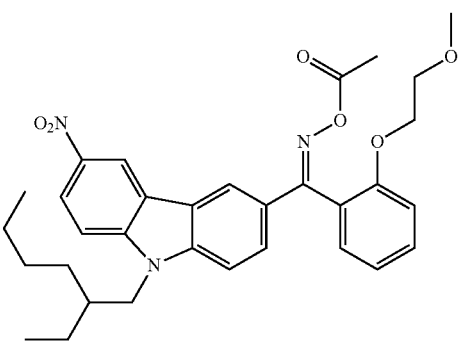

-continued
Compound No. 56
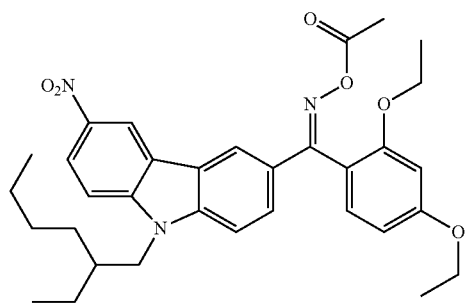
[Formula 8]
Compound No. 57
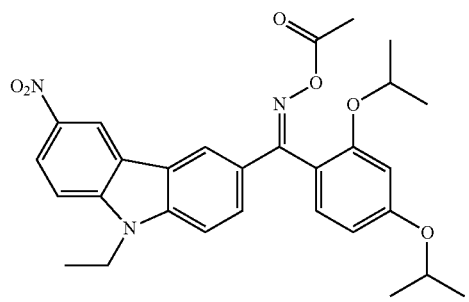
Compound No. 58
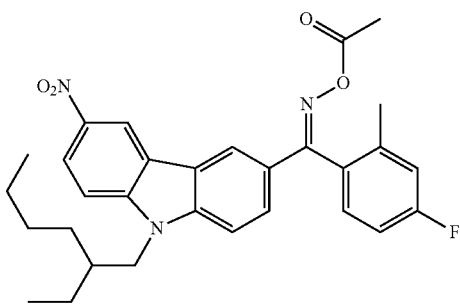
Compound No. 59
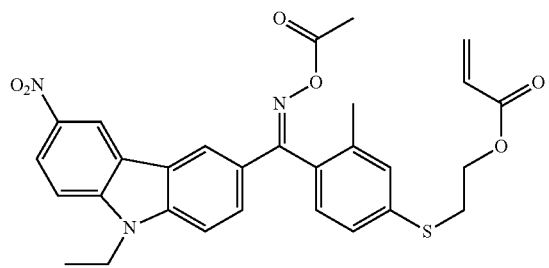
Compound No. 60
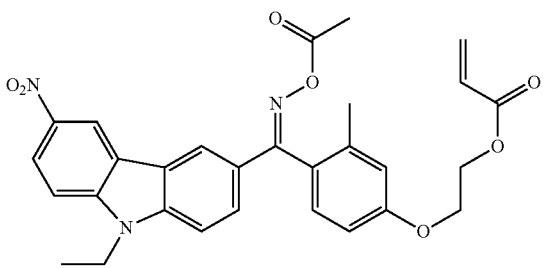
Compound No. 61
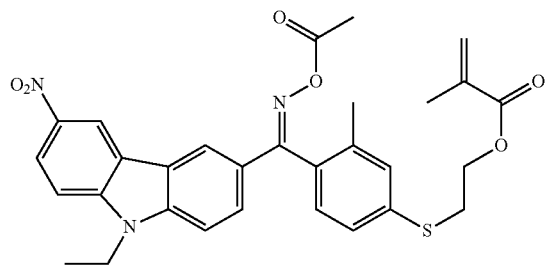
Compound No. 62
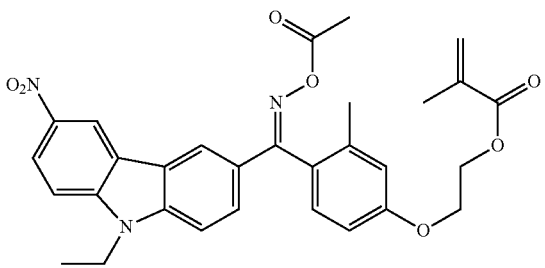
Compound No. 63
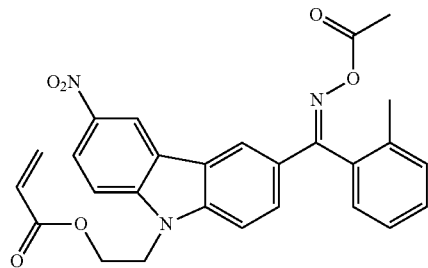
Compound No. 64
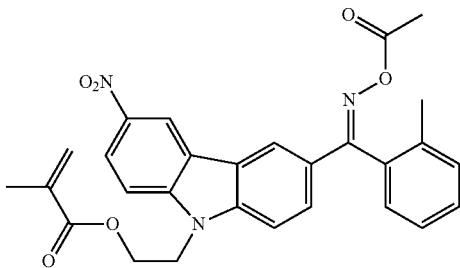

-continued
Compound No. 65
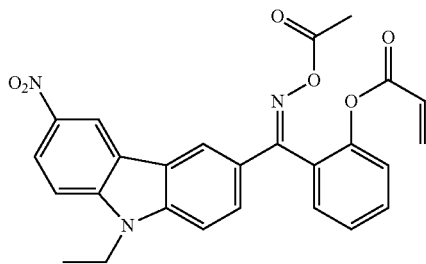
Compound No. 66
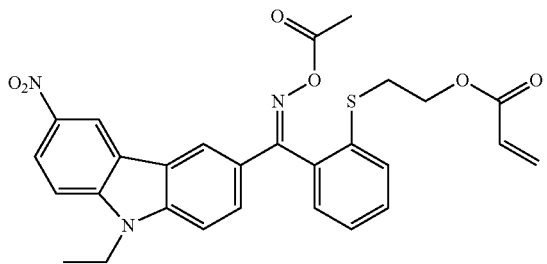
Compound No. 67
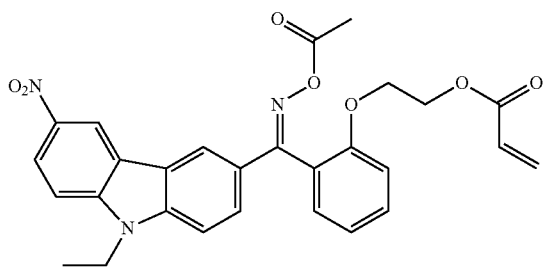
[Formula 9]
Compound No. 68
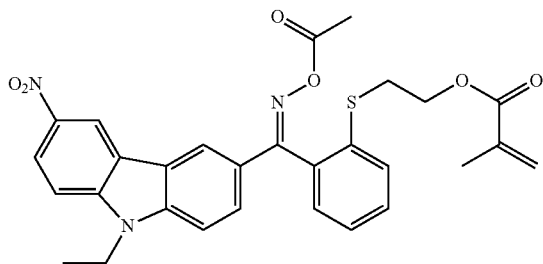
Compound No. 69
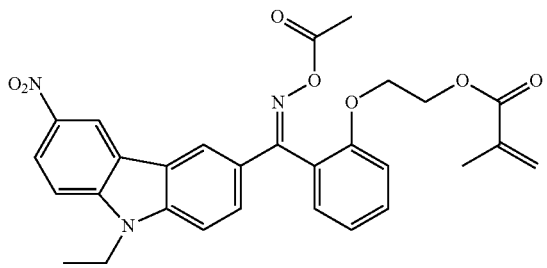
Compound No. 70
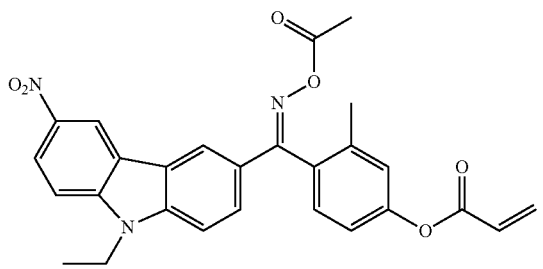
Compound No. 71
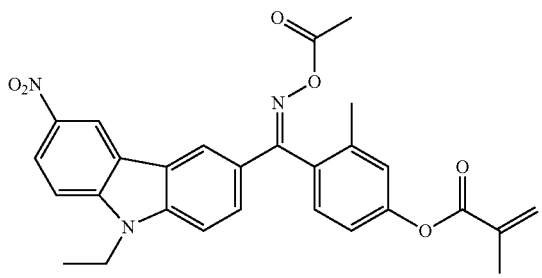

The oxime ester compound of general formula (I) is prepared by, for example, the following process in accordance with reaction scheme:

A nitrocarbazole compound 1 and an acid chloride 2 are allowed to react in the presence of zinc chloride to give an acylated compound 3. The acylated compound 3 is allowed to react with hydroxylamine hydrochloride in the presence of DMF to give an oxime compound 4. The oxime compound 4 is allowed to react with an acid anhydride 5 or an acid chloride 5' to yield an oxime ester compound of general formula (I).

[Formula 10]

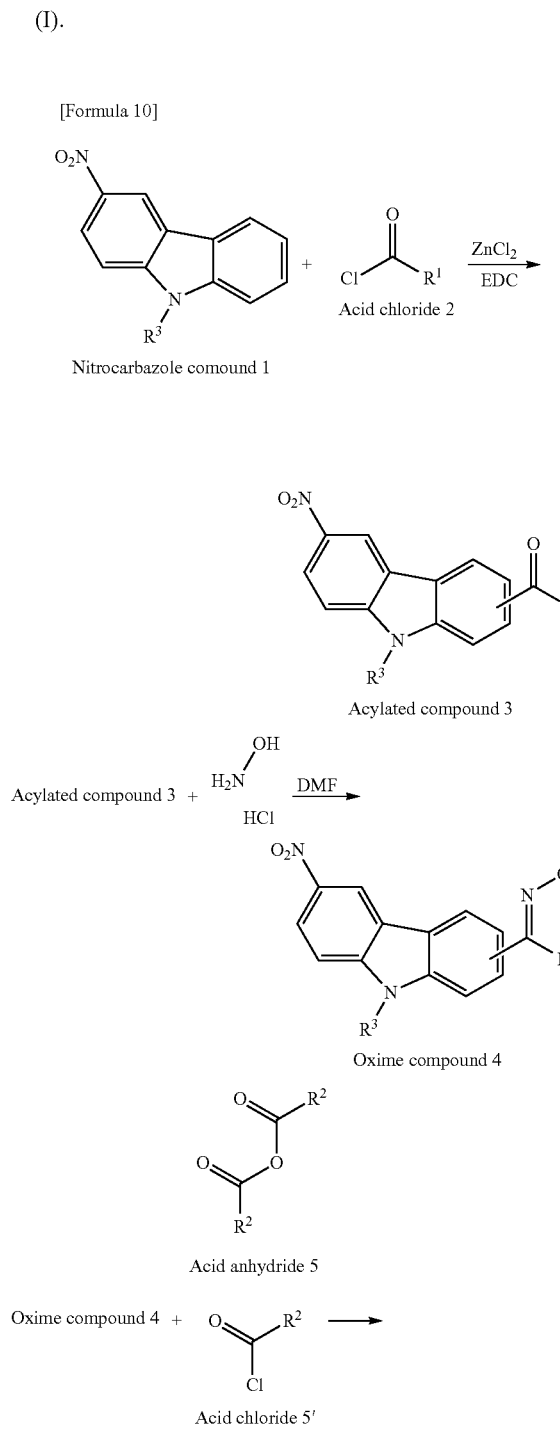

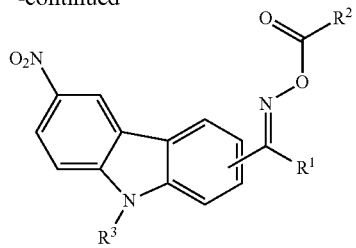

Oxime ester compound of general formula (I)

The oxime ester compound of the invention is useful as an initiator for photopolymerization of a polymerizable compound having an ethylenically unsaturated bond.

The photosensitive composition according to the invention will then be described. The photosensitive composition of the invention contains a photopolymerization initiator having the oxime ester compound as an active ingredient, an ethylenically unsaturated polymerizable compound, and, if desired, an inorganic compound and/or a colorant, and other optional components such as a solvent.

Any ethylenically unsaturated polymerizable compound that has been used in a photosensitive composition can be used in the invention. Examples include unsaturated aliphatic hydrocarbons, such as ethylene, propylene, butylene, isobutylene, vinyl chloride, vinylidene chloride, vinylidene fluoride, and tetrafluoroethylene; a polymer having a carboxyl group and a hydroxyl group at both terminals, such as (meth)acrylic acid, α-chloroacrylic acid; itaconic acid, maleic acid, citraconic acid, fumaric acid, hymic acid, crotonic acid, isocrotonic acid, vinylacetic acid, allylacetic acid, cinnamic acid, sorbic acid, mesaconic acid, trimellitic acid, pyromellitic acid, 2,2',3,3'-benzophenonetetracarboxylic acid, 3,3,4,4'-benzophenonetetracarboxylic acid, mono[2-(meth)acryloyloxyethyl]succinate, mono[2-(meth)acryloyloxyethyl]phthalate, a mono(methacrylate) and ω-carboxypolycaprolactone mono(meth)acrylate; unsaturated polybasic acids such as hydroxyethyl (meth)acrylate malate, hydroxypropyl (meth)acrylate malate, dicyclopentadiene malate, and a polyfunctional (meth)acrylate having one carboxyl group and two or more (meth)acryloyl groups; esters between an unsaturated monobasic acid and a polyhydric alcohol or a polyhydric phenol, such as 2-hydroxyethyl (meth)acrylate, 2-hydroxypropyl (meth)acrylate, glycidyl (meth)acrylate, compound Nos. 72 to 75 shown below, methyl (meth)acrylate, butyl (meth)acrylate, isobutyl (meth)acrylate, t-butyl (meth)acrylate, cyclohexyl (meth)acrylate, n-octyl (meth)acrylate, isooctyl (meth)acrylate, isononyl (meth)acrylate, stearyl (meth)acrylate, lauryl (meth)acrylate, methoxyethyl (meth)acrylate, dimethylaminomethyl (meth)acrylate, dimethylaminoethyl (meth)acrylate, aminopropyl (meth)acrylate, dimethylaminopropyl (meth)acrylate, ethoxyethyl (meth)acrylate, poly(ethoxy)ethyl (meth)acrylate, butoxyethoxyethyl (meth)acrylate, ethylhexyl (meth)acrylate, phenoxyethyl (meth)acrylate, tetrahydrofuryl (meth)acrylate, vinyl (meth)acrylate, allyl (meth)acrylate, benzyl (meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol penta(meth)acrylate, dipentaerythritol hexa(meth)acrylate, pentaerythritol penta(meth)acrylate, pentaerythritol tetra(meth)acrylate, pentaerythritol tri(meth)acrylate, tricyclodecanedimethylol di(meth)acrylate, tri[(meth)acryloylethyl]isocyanurate, and polyester (meth)acrylate oligomers; metal salts of unsaturated polybasic acids, such as zinc (meth)acrylate and magnesium (meth) acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydrides, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride; amides formed between an unsaturated monobasic acid and a polyfunctional amine, such as (meth)acrylamide, methylenebis(meth)acrylamide, diethylenetriaminetris(meth)acrylamide, xylylenebis(meth)acrylamide, α-chloroacrylamide, and N-2-hydroxyethyl (meth)acrylamide; unsaturated aldehydes, such as acrolein; unsaturated nitriles, such as (meth)acrylonitrile, α-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones, such as methyl vinyl ketone; unsaturated amine compounds, such as vinylamine, allylamine, N-vinylpyrrolidone, and vinylpiperidine; vinyl alcohols, such as allyl alcohol and crotyl alcohol; vinyl ethers, such as vinyl methyl ether, vinyl ethyl ether, n-butyl vinyl ether, isobutyl vinyl ether, and allyl glycidyl ether; unsaturated imides, such as maleimide, N-phenylmaleimide, and N-cyclohexylmaleimide; indenes, such as indene and 1-methylindene; aliphatic conjugated dienes, such as 1,3-butadiene, isoprene, and chloroprene; macromonomers having a mono(meth)acryloyl group at the terminal of a polymeric molecular chain, such as polystyrene, polymethyl (meth)acrylate, poly-n-butyl (meth)acrylate, and polysiloxanes; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine, vinylurethane compounds formed between a hydroxyl-containing vinyl monomer and a polyisocyanate compound, and vinylepoxy compounds formed between a hydroxyl-containing vinyl monomer and a polyepoxy compound. Of these ethylenically unsaturated polymerizable compounds, a (mono)methacrylate of a polymer having a carboxyl group and a hydroxyl group at both terminals, a polyfunctional (meth)acrylate having one carboxyl group and two or more (meth)acryloyl groups, and an ester between an unsaturated monobasic acid and a polyhydric alcohol or polyhydric phenol are suited to be polymerized by using the photopolymerization initiator containing the oxime ester compound of the invention as an active ingredient.

The polymerizable compounds may be used either individually or as a mixture of two or more thereof. The two or more polymerizable compounds to be used in combination may be in the form of a copolymer previously prepared therefrom.

[Formula 11]

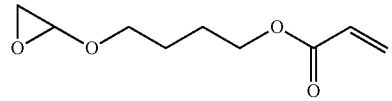

Compound No. 72

[Formula 12]

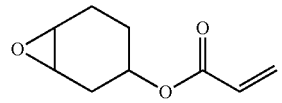

Compound No. 73

[Formula 13]

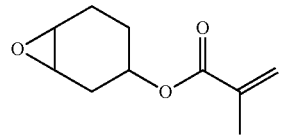

Compound No. 74

[Formula 14]

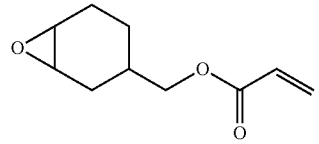

Compound No. 75

When the ethylenically unsaturated polymerizable compound is an ethylenically unsaturated, alkali-developable compound, the photosensitive composition of the invention serves as an alkali-developable photosensitive resin composition. Examples of the ethylenically unsaturated, alkali-developable compound include acrylic ester copolymers, phenol and/or cresol novolak epoxy resins, polyphenylmethane epoxy resins having two or more epoxy groups, and resins obtained by causing an epoxy compound, such as a compound represented by general formula (II) below, and an unsaturated monobasic acid to react with each other and causing the resulting reaction product to react with a polybasic acid anhydride. Preferred of them are resins obtained by causing an epoxy compound, such as a compound represented by general formula (II) below, and an unsaturated monobasic acid to react with each other and causing the resulting product to react with a polybasic acid anhydride. The ethylenically unsaturated, alkali-developable compound preferably contains 0.2 to 1.0 equivalents of an unsaturated group.

[Formula 15]

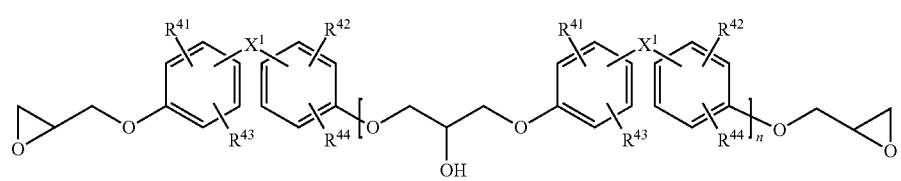

(II)

wherein $X^1$ represents a single bond, a methylene group, a halogen-substituted or unsubstituted alkylidene group having 1 to 4 carbon atoms, an alicyclic hydrocarbon group having 3 to 20 carbon atoms, O, S, $SO_2$, SS, SO, CO, OCO, or a substituent represented by [formula 16] or [formula 17] shown below; $R^{41}$, $R^{42}$, $R^{43}$, and $R^{44}$ each independently represent a hydrogen atom, a halogen-substituted or unsubstituted alkyl group having 1 to 5 carbon atoms, a halogen-substituted or unsubstituted alkoxy group having 1 to 8 carbon atoms, a halogen-substituted or unsubstituted alkenyl group having 2 to 5 carbon atoms, or a halogen atom; and m represents an integer of 0 to 10.

[Formula 16]

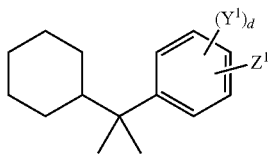

wherein $Y^1$ represents a hydrogen atom, a phenyl group which may be substituted with an alkyl group having 1 to 10 carbon atoms or an alkoxy group having 1 to 10 carbon atoms, or a cycloalkyl group having 3 to 10 carbon atoms; $Z^1$ represents a halogen-substituted or unsubstituted alkyl group having 1 to 10 carbon atoms, a halogen-substituted or unsubstituted alkoxy group having 1 to 10 carbon atoms, a halogen-substituted or unsubstituted alkenyl group having 2 to 10 carbon atoms, or a halogen atom; and d represents an integer of 0 to 5.

[Formula 17]

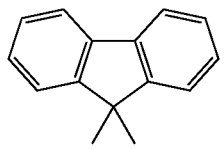

Examples of the unsaturated monobasic acid which is caused to react on the epoxy compound include acrylic acid, methacrylic acid, crotonic acid, cinnamic acid, sorbic acid, hydroxyethyl methacrylate malate, hydroxyethyl acrylate malate, hydroxypropyl methacrylate malate, hydroxypropyl acrylate malate, and dicyclopentadiene malate. Examples of the polybasic acid anhydride that is caused to react after the reaction of the unsaturated monobasic acid include biphenyltetracarboxylic acid dianhydride, tetrahydrophthalic anhydride, succinic anhydride, biphthalic anhydride, maleic anhydride, trimellitic anhydride, pyromellitic anhydride, 2,2',3,3'-benzophenonetetracarboxylic acid anhydride, ethylene glycol bisanhydrotrimellitate, glycerol trisanhydrotrimellitate, hexahydrophthalic anhydride, methyltetrahydrophthalic anhydride, nadic anhydride, methylnadic anhydride, trialkyltetrahydrophthalic anhydrides, hexahydrophthalic anhydride, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride.

The epoxy compound and the unsaturated monobasic acid are preferably used in such a molar ratio that results in the formation of an epoxy adduct having 0.1 to 1.0 carboxyl group of the unsaturated monobasic acid added per epoxy group of the epoxy compound. The polybasic acid anhydride is preferably used in such a molar ratio as to provide 0.1 to 1.0 acid anhydride structure per hydroxyl group of the resulting epoxy adduct.

The reactions of the epoxy compound, unsaturated monobasic acid, and polybasic acid anhydride are carried out in a usual manner.

In order to improve developability of the alkali-developable photosensitive resin composition, either colored or not colored, the acid value of the ethylenically unsaturated alkali-developable compound may be adjusted by using a mono- or polyfunctional epoxy compound in combination with the ethylenically unsaturated, alkali-developable compound. It is preferred that the solid content of the ethylenically unsaturated, alkali-developable compound to have an acid value of 5 to 120 mg-KOH/g. The amount of the mono- or polyfunctional epoxy compound to be used is preferably chosen so as to satisfy the above recited range of acid value.

Examples of the monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenyl glycidyl ether, cresyl glycidyl ether, 2-methylcresyl glycidyl ether, 4-nonylphenyl glycidyl ether, benzyl glycidyl ether, p-cumylphenyl glycidyl ether, trimethyl glycidyl ether, 2,3-epoxypropyl methacrylate, epoxidized soybean oil, epoxidized linseed oil, glycidyl butyrate, vinylcyclohexene monoxide, 1,2-epoxy-4-vinylcyclohexane, styrene oxide, pinene oxide, methylstyrene oxide, cyclohexene oxide, propylene oxide, and compound Nos. 76 and 77 below.

[Formula 18]

Compound No. 76

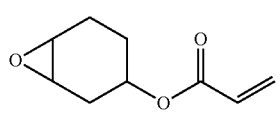

[Formula 19]

Compound No. 77

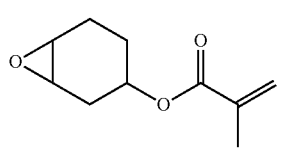

The polyfunctional epoxy compound is preferably at least one compound selected from the group consisting of bisphenol epoxy compounds and glycidyl ethers.

Using at least one of them is effective in providing a (colored) alkali developable photosensitive resin composition having further improved characteristics. Examples of the bisphenol epoxy compounds include the epoxy compounds represented by general formula (II) and others including hydrogenated bisphenol epoxy compounds. Examples of the glycidyl ethers include ethylene glycol diglycidyl ether, propylene glycol diglycidyl ether, 1,4- butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane.

Other useful polyfunctional epoxy compounds include novolak epoxy compounds, such as phenol novolak epoxy compounds, biphenyl novolak epoxy compounds, cresol novolak epoxy compounds, bisphenol A novolak epoxy compounds, and dicyclopentadiene novolak epoxy compounds; alicyclic epoxy compounds, such as 3,4-epoxy-6-methylcyclohexylmethyl-3,4-epoxy-6-methylcyclohexanecarboxylate, 3,4-epoxycyclohexylmethyl-3,4-epoxycyclohexanecarboxylate, and 1-epoxyethyl-3,4-epoxycyclohexane; glycidyl esters, such as diglycidyl phthalate, diglycidyl tetrahydrophthalate, and glycidyl dimerate; glycidylamines, such as tetraglycidyl diaminodiphenylmethane, triglycidyl p-aminophenol, and N,N-diglycidylaniline; heterocyclic epoxy compounds, such as 1,3-diglycidyl-5,5-dimethylhydantoin and triglycidyl isocyanurate; dioxide compounds, such as dicyclopentadiene dioxide; naphthalene epoxy compounds, triphenylmethane epoxy compounds, and dicyclopentadiene epoxy compounds.

The amount of the photopolymerization initiator to be used in the photosensitive composition of the invention is preferably, but not limited to, 1 to 70 parts, more preferably 1 to 50 parts, even more preferably 5 to 30 parts, by mass per 100 parts by mass of the ethylenically unsaturated polymerizable compound.

In the case when the photosensitive composition is contemplated to be a (colored) alkali developable photosensitive resin composition, the content of the ethylenically unsaturated, alkali developable compound in the composition is preferably 1 to 20%, more preferably 3 to 12%, by mass.

The photosensitive composition of the invention may optionally contain a solvent. Usually, solvents capable of dissolving or dispersing the above described components (such as the oxime ester compound of the invention and the ethylenically unsaturated polymerizable compound) are used where necessary. Such solvents include ketones, e.g., methyl ethyl ketone, methyl amyl ketone, diethyl ketone, acetone, methyl isopropyl ketone, methyl isobutyl ketone, and cyclohexanone; ethers, such as ethyl ether, dioxane, tetrahydrofuran, 1,2-dimethoxyethane, 1,2-diethoxyethane, and dipropylene glycol dimethyl ether; esters, such as methyl acetate, ethyl acetate, n-propyl acetate, isopropyl acetate, and n-butyl acetate; cellosolve solvents, such as ethylene glycol monomethyl ether, ethylene glycol monoethyl ether, and propylene glycol-1-monoethyl ether-2-acetate;; alcohols, such as methanol, ethanol, isopropyl alcohol, n-propanol, isobutanol, n-butanol, and amyl alcohol; ethers, such as ethylene glycol monomethyl acetate, ethylene glycol monoethyl acetate, and propylene glycol methyl acetate; BTX solvents (benzene, toluene, xylene, etc.); aliphatic hydrocarbons, such as hexane, heptane, octane, and cyclohexane; terpene hydrocarbon oils, such as turpentine oil, D-limonene, and pinene; paraffinic solvents, such as mineral spirit, Swazol #310 (available from Cosmo Matsuyama Oil Co., ltd.), and Solvesso #100 (available from Exxon Chemical); halogenated aliphatic hydrocarbons, such as carbon tetrachloride, chloroform, trichloroethylene, methylene chloride, and 1,2-dichloroethane; halogenated aromatic hydrocarbons, such as chlorobenzene; carbitol solvents, aniline, triethylamine, pyridine, acetic acid, acetonitrile, carbon disulfide, N,N-dimethylformamide, N-methylpyrrolidone, dimethyl sulfoxide, and water. These solvents may be used either individually or as a mixture of two or more thereof.

Preferred of them are ketones and cellosolve solvents, particularly propylene glycol-1-monomethyl ether-2-acetate, cyclohexanone, and so on in view of providing good compatibility between a resist and a photopolymerization initiator in a photosensitive composition.

The photosensitive composition may further contain an inorganic compound. Examples of the inorganic compound include metal oxides, such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt compounds, manganese compounds, glass powder, mica, talc, kaolin, ferrocyanides, various metal sulfates, sulfides, selenides, aluminum silicate, calcium silicate, aluminum hydroxide, platinum, gold, silver, and copper. Preferred of them are titanium oxide, silica, layered clay minerals, and silver. The inorganic compound content in the photosensitive composition is preferably 0.1 to 50 parts, more preferably 0.5 to 20 parts, by mass per 100 parts by mass of the ethylenically unsaturated polymerizable compound. The inorganic compounds may be used either individually or in combination of two or more thereof.

The inorganic compounds are used as, for example, a filler, an antireflection agent, an electrically conductive agent, a stabilizer, a flame retardant, a mechanical strength improving agent, a specific wavelength absorbing agent, an ink repellent agent, and the like.

The photosensitive composition of the invention, especially the alkali developable photosensitive resin composition may further contain a colorant to be formulated into a colored photosensitive composition. Pigments, dyes, and naturally occurring dyes are used as a colorant. The colorants may be used either individually or as a mixture of two or more thereof.

The pigments may be either organic or inorganic, including nitroso compounds, nitro compounds, azo compounds, diazo compounds, xanthene compounds, quinoline compounds, anthraquinone compounds, coumarin compounds, phthalocyanine compounds, isoindolinone compounds, isoindoline compounds, quinacridone compounds, anthanthrone compounds, perynone compounds, perylene compounds, diketopyrrolopyrrole compounds, thioindigo compounds, dioxazine compounds, triphenylmethane compounds, quinophthalone compounds, and naphthalenetetracarboxylic acids; metal complex compounds, such as azo dyes, and cyanine dyes; lake pigments; carbon black species, such as furnace black, channel black, thermal black, acetylene black, Ketjen black, and lamp black; the carbon blacks recited which have been surface treated with an acid or an alkali; graphite, graphitized carbon black, activated carbon, carbon fiber, carbon nanotube, carbon microcoil, carbon nanohorn, carbon aerogel, fullerene; aniline black, pigment black 7, titanium black; hydrophobic resins, chromium oxide green, Milori blue, cobalt green, cobalt blue, manganese compounds, ferrocyanides, phosphate ultramarine blue, Prussian blue, ultramarine, cerulean blue, viridian, emerald green, lead sulfate, lead yellow, zinc yellow, Bengal red (red iron (III) oxide), cadmium red, synthetic iron black, and amber. The pigments may be used either individually or as a mixture thereof.

Commercially available pigments may be used, including pigment red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; pigment orange 13, 31, 34, 36, 38, 43, 46, 48, 49, 51, 52, 55, 59, 60, 61, 62, 64, 65, and 71; pigment yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; pigment green 7, 10, and 36; pigment blue 15, 15:1, 15:2, 15:3, 15:4, 15:5, 15:6, 22, 24, 56, 60, 61, 62, and 64; and pigment violet 1, 19, 23, 27, 29, 30, 32, 37, 40, and 50.

Examples of the dyes include azo dyes, anthraquinone dyes, indigoid dyes, triarylmethane dyes, xanthene dyes, alizarine dyes, acridine dyes, stilbene dyes, thiazole dyes, naphthol dyes, quinoline dyes, nitro dyes, indamine dyes, oxazine dyes, phthalocyanine dyes, and cyanine dyes. The may be used as a mixture thereof.

The amount of the colorant to be added to the photosensitive composition is preferably 50 to 350 parts, more preferably 100 to 250 parts, by mass per 100 parts by mass of the ethylenically unsaturated polymerizable compound.

The photosensitive composition may further contain other organic polymer in addition to the ethylenically unsaturated polymerizable compound to provide a cured product with improved characteristics. Examples of the organic polymer include polystyrene, polymethyl methacrylate, methyl methacrylate-ethyl acrylate copolymers, poly(meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonate, polyvinyl butyral, cellulose esters, polyacrylamide, saturated polyesters, phenol resins, phenoxy resins, polyamide-imide resins, polyamic acid resins, and epoxy resins. Preferred of them are polystyrene, (meth) acrylic acid-methyl acrylate copolymers, and epoxy resins.

The amount of the other organic polymer is preferably 10 to 500 parts by mass per 100 parts by mass of the ethylenically unsaturated polymerizable compound.

The photosensitive composition may furthermore contain a monomer having an unsaturated bond, a chain transfer agent, a surfactant, and so on.

Examples of the monomer having an unsaturated bond include 2-hydroxyethyl acrylate, 2-hydroxypropyl acrylate, isobutyl acrylate, n-octyl acrylate, isooctyl acrylate, isononyl acrylate, stearyl acrylate, methoxyethyl acrylate, dimethylaminoethyl acrylate, zinc acrylate, 1,6-hexanediol diacrylate, trimethylolpropane triacrylate, 2-hydroxyethyl methacrylate, 2-hydroxypropyl methacrylate, butyl methacrylate, t-butyl methacrylate, cyclohexyl methacrylate, trimethylolpropane trimethacrylate, dipentaerythritol pentaacrylate, dipentaerythritol hexaacrylate, pentaerythritol tetraacrylate, pentaerythritol triacrylate, bisphenol A diglycidyl ether (meth)acrylate, bisphenol F diglycidyl ether (meth)acrylate, bisphenol Z diglycidyl ether (meth)acrylate, and tripropylene glycol di(meth)acrylate.

Examples of the chain transfer agent include mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl) glycine, 2-mercaptonicotinic acid, 3-[N-(2-mercaptoethyl) carbamoyl]propionic acid, 3-[N-(2-mercaptoethyl)amino] propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the recited mercapto compounds; and iodized alkyl compounds, such as iodoacetic acid, iodopropionic acid, 2-iodoethanol, 2-iodoethanesulfonic acid, and 3-iodopropanesulfonic acid.

Examples of the surfactant include fluorine-containing surfactants, such as perfluoroalkylphosphoric esters, perfluoroalkylcarboxylic acid salts; anionic surfactants, such as higher fatty acid alkali salts, alkylsulfonic acid salts, and alkylsulfuric acid salts; cationic surfactants, such as higher amine halogenic acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants, and silicone surfactants. These surfactants may be used in combination thereof.

If desired, the photosensitive composition may contain other photopolymerization initiator or sensitizer in addition to the oxime ester compound of the invention. A combined use of other photopolymerization initiator can produce marked synergistic effects.

Any known photopolymerization initiators can be used in combination with the oxime ester compound. Examples of such initiators include benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4',5'-tetraphenyl-1,2'-biimidazole, 4,4-azobisisobutyronitrile, triphenylphosphine, camphorquinone; N-1414, N-1717, N-1919, and PZ-408 (from ADEKA Corp.); Irgacure 369, Irgacure 907, Irgacure OXE 01, and Irgacure OXE 02 (from Ciba Specialties Chemicals Corp.); benzoyl peroxide, and compounds represented by general formulae (III) to (V) shown below. These photopolymerization initiators can be used either individually or in a combination of two or more thereof. The amount of the known photopolymerization initiator(s), if used, is preferably equal to or less than the mass of the oxime ester compound of the invention.

[Formula 20]

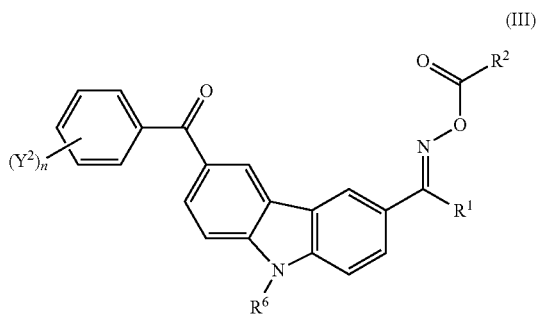

wherein $R^1$ and $R^2$ are as defined for general formula (I); $R^6$ has the same meaning as $R^1$; $Y^2$ represents a halogen atom or an alkyl group; and n represents 0 to 5.

[Formula 21]

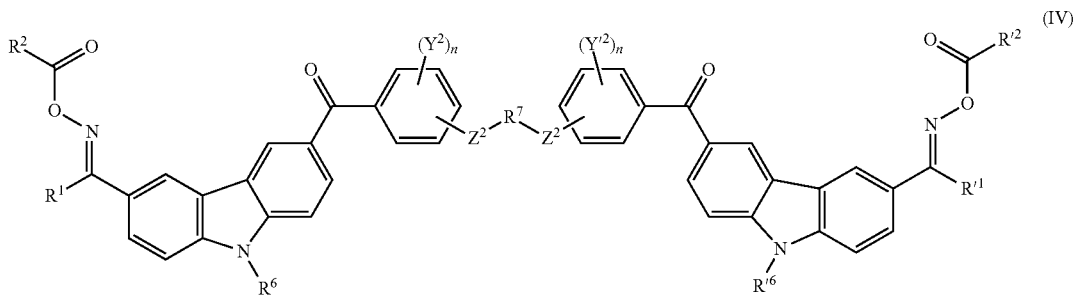

wherein $R^1$ and $R^2$ are as defined for general formula (I); $R^6$, $Y^2$ and n are as defined for general formula (III); $R'^1$, $R'^2$, and $R'^6$ have the same meaning as $R^1$; $Y'^2$ has the same meaning as $Y^2$; $R^7$ represents a diol residue or a dithiol residue; and $Z^2$ represents an oxygen atom or a sulfur atom.

[Formula 22]

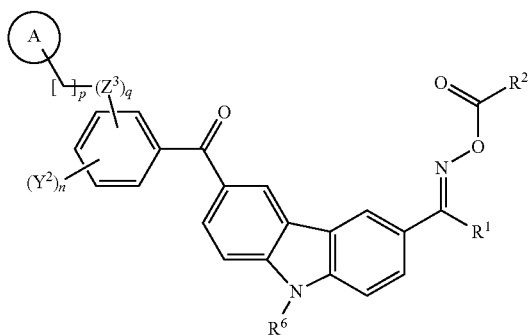

wherein $R^1$ and $R^2$ are as defined for general formula (I); $R^6$, $Y^2$, and n are as defined for general formula (III); $Z^3$ represents an oxygen atom, a sulfur atom, or a selenium atom; A represents a heterocyclic group; p represents an integer of 0 to 5; and q is 0 or 1.

If desired, the photosensitive composition of the present invention may contain commonly used additives, including thermal polymerization inhibitors (e.g., p-anisole, hydroquinone, pyrocatechol, t-butylcatechol, and phenothiazine), plasticizers, adhesion accelerators, fillers, defoaming agents, leveling agents, surface modifiers, antioxidants, ultraviolet absorbers, dispersing acids, anti-coagulants, catalysts, effect accelerators, sensitizers, crosslinking agents, and thickeners.

The amounts of the optional components other than the ethylenically unsaturated polymerizable compound and the oxime ester compound, except the above described other photopolymerization initiator, inorganic filler, colorant, and solvent, in the photosensitive composition are decided as appropriate to the use of the composition. Preferably, the total amount of the optional components is not more than 50 parts by mass per 100 parts by mass of the ethylenically unsaturated polymerizable compound.

The photosensitive composition of the invention is applied to a substrate, such as soda glass, quartz glass, semiconductor substrates, metals, paper, or plastics. The method of application is not limited. Any known coating methods may be used, such as spin coating, roll coating, bar coating, die coating, curtain coating, printing, and dipping. The photosensitive composition may be once applied to a carrier substrate, such as a film, and then transferred to another substrate.

The photosensitive composition of the invention has unlimited application. It finds use in, for example, photocuring paints or varnishes, photocuring adhesives, printed boards; color filters for liquid crystal color display devices, such as TV monitors, PC monitors, personal digital assistances, and digital cameras; electrode materials for plasma display panels; powder coatings, printing inks, printing plates, adhesives, compositions for dental use, gel coats, photoresists for electronics, electroplating resists, etching resists, liquid and dry films, soldering resists; resists for producing color filters of various displays or for forming structures in the production of plasma display panels, electroluminescent displays, and LCDs; encapsulating compositions for electric/electronic components, magnetic recording materials, fine machine parts, waveguides, optical switches, plating masks, etching masks, color test systems, glass fiber cable coatings, screen printing stencils, materials for making a three-dimensional object by stereolithography, holographic recording materials, image recording materials, fine electronic circuits, decolorizing materials, decolorizing materials for image recording materials, decolorizing materials for image recording materials using microcapsules, photoresist materials for printed wiring boards, photoresist materials for direct image writing using UV and visible lasers, and photoresist materials or protective layers used to form dielectric layers in the fabrication of multilayered printed circuit boards.

The photosensitive composition containing the oxime ester compound of the invention can be cured with active light from light sources emitting light of wavelengths of from 300 to 450 nm. Such light sources include an ultrahigh pressure mercury lamps, mercury vapor arcs, carbon arcs, and xenon arcs.

EXAMPLES

The present invention will now be illustrated in greater detail with reference to Examples, but it should be understood that the invention is not deemed to be limited thereto.

Examples 1-1 to 1-22

Preparation of Compound Nos. 1 to 3, 7, 10, 12, 20, 33, 45 to 51, and 53 to 58

Step 1-Preparation of Acylated Compound

In a nitrogen atmosphere, 10.4 g (78 mmol) of aluminum chloride and 33.0 g of dichloroethane were put in a reactor. In the same atmosphere, 36 mmol of an acid chloride and then 30 mmol of a nitrocarbazole compound and 33.0 g of dichloroethane were added slowly while cooling with ice, followed by stirring at 5° C. for 30 minutes. The reaction mixture was poured into ice-water for oil-water separation. The solvent was removed to give a desired acylated compound.

Step 2-Preparation of Compound Nos. 1 to 3, 7, 10, 12, 20, 33, 45 to 51, and 53 to 58

In a reactor were charged 20 mmol of the acylated compound obtained in step (1), 2.1 g (30 mmol) of hydroxylamine hydrochloride, and 16.9 g of dimethylformamide and stirred at 80° C. for 1 hour in a nitrogen stream. The reaction system was cooled to room temperature, followed by oil-water separation. The solvent was removed by evaporation. To the residue were added 25.4 g of butyl acetate and then 2.45 g (24 mmol) of acetic anhydride. The mixture was stirred at 90° C. for 1 hour, followed by cooling to room temperature. The reaction mixture was neutralized with a 5% sodium hydroxide aqueous solution, followed by oil-water separation, followed by solvent removal, followed by recrystallization from ethyl acetate to yield compound Nos. 1 to 3, 7, 10, 12, 20, 33, 45 to 51, and 53 to 58. The analytical results of the resulting compounds are shown in Tables 1 to 3. With respect to compound No. 49, two isomers were separately isolated so that analytical results for each of them are shown. With respect to compound Nos. 53 and 54, the isomers gave different results only in the NMR analysis as shown in Table 3.

TABLE 1

| | Oxime Ester Compound | $\lambda_{max}$*[1] (nm) | Melting Point (° C.) | Decomp. Point (° C.) | Solubility PGM-Ac*[2] (%) | Solubility CHN*[3] (%) |
|---|---|---|---|---|---|---|
| Example 1-1 | Compound No. 1 | 277,372 | 125.1 | 278.3 | 4.1 | 18.9 |
| Example 1-2 | Compound No. 2 | 272,373 | 126.9 | 262.2 | 1.4 | 9.2 |
| Example 1-3 | Compound No. 3 | 272,371 | 204.9 | 263.9 | 0.12 | 0.80 |
| Example 1-4 | Compound No. 7 | 275,370 | 152.4 | 258.0 | 0.38 | 2.4 |
| Example 1-5 | Compound No. 10 | 261,272,362 | 205.1 | 257.1 | 0.091 | 0.54 |
| Example 1-6 | Compound No. 12 | 275,372 | 67.3 | 281.0 | 25 | 31 |
| Example 1-7 | Compound No. 20 | 273,365 | 158.0 | 264.3 | 0.16 | 3.7 |
| Example 1-8 | Compound No. 33 | 280,372 | 140.9 | 272.8 | 5.1 | 27 |
| Example 1-9 | Compound No. 45 | 272,374 | 107.2 | 277.8 | 0.4 | 7.2 |
| Example 1-10 | Compound No. 46 | 271,374 | 92.7 | 261.3 | 0.5 | 5.0 |
| Example 1-11 | Compound No. 47 | 275,373 | 98.1 | 271.7 | 0.3 | 5.3 |
| Example 1-12 | Compound No. 48 | 275,374 | 85.5 | 245.9 | 5.0 | 42 |
| Example 1-13 | Compound No. 49(1) | 279,378 | 176.1 | 277.4 | 0.49 | 5.3 |
| Example 1-14 | Compound No. 49(2) | 279,369 | 150.9 | 288.2 | 1.0 | 6.8 |
| Example 1-15 | Compound No. 50 | 276,373 | 77.3 | 248.5 | 6.0 | 45 |
| Example 1-16 | Compound No. 51 | 267,373 | 142.4 | 256.6 | 1.5 | 13 |
| Example 1-17 | Compound No. 53 | 276,378 | 147.1 | 280.1 | 5.0 | 24 |
| Example 1-18 | Compound No. 54 | 279,373 | oil | 258.9 | 20 | 14 |
| Example 1-19 | Compound No. 55 | 283,373 | 152.5 | 302.4 | 1.2 | 3.2 |
| Example 1-20 | Compound No. 56 | 282,375 | 137.1 | 283.5 | 3.6 | 23 |

TABLE 1-continued

|  | Oxime Ester Compound | $\lambda_{max}$*1 (nm) | Melting Point (°C.) | Decomp. Point (°C.) | Solubility PGM-Ac*2 (%) | Solubility CHN*3 (%) |
|---|---|---|---|---|---|---|
| Example 1-21 | Compound No. 57 | 280,373 | 164.0 | 275.5 | 2.4 | 12 |
| Example 1-22 | Compound No. 58 | 283,372 | 153.4 | 269.3 | 1.2 | 7.6 |

*1 CHCl₃ was used as a solvent.
*2 PGM-Ac: Propylene glycol-1-monomethyl ether-2-acetate
*3 CHN: Cyclohexane

TABLE 2

|  | Oxime Ester Compound | IR Absorption Spectrum (cm⁻¹) |
|---|---|---|
| Example 1-1 | Compound No. 1 | 2958, 2930, 2872, 1766, 1631, 1600, 1513, 1485, 1459, 1366, 1328, 1223, 1203, 1152, 1135, 1092, 984, 931, 879, 823, 749, 728 |
| Example 1-2 | Compound No. 2 | 2928, 2858, 1765, 1633, 1600, 1506, 1488, 1368, 1323, 1203, 1153, 1137, 1092, 984, 930, 883, 822, 807, .751, 727, 648 |
| Example 1-3 | Compound No. 3 | 2980, 1766, 1630, 1599, 1488, 1458, 1377, 1339, 1316, 1277, 1209, 1200, 1152, 1130, 1094, 1004, 983, 935, 912, 884, 806, 750, 717, 645 |
| Example 1-4 | Compound No. 7 | 2971, 2864, 1769, 1600, 1509, 1487, 1362, 1321, 1266, 1223, 1156, 1330, 1114, 1094, 1049, 1021, 931, 888, 843, 811, 750, 717 |
| Example 1-5 | Compound No. 10 | 2941, 1762, 1744, 1630, 1601, 1508, 1489, 1459, 1375, 1330, 1308, 1205, 1159, 1136, 1096, 1009, 984, 888, 819, 751, 729 |
| Example 1-6 | Compound No. 12 | 3090, 2979, 2935, 2360, 2342, 1765, 1732, 1631, 1599, 1513, 1487, 1458, 1368, 1330, 1263, 1203, 1155, 1136, 1094, 1004, 983, 936, 885, 817, 751, 728 |
| Example 1-7 | Compound No. 20 | 2924, 2851, 1764, 1719, 1635, 1604, 1513, 1484, 1458, 1410, 1362, 1321, 1303, 1200, 1136, 1092, 1005, 943, 886, 864, 816, 747, 728, 682 |
| Example 1-8 | Compound No. 33 | 2979, 1765, 1604, 1514, 1484, 1365, 1328, 1275, 1234, 1201, 1096, 1006, 922, 823, 751, 649 |
| Example 1-9 | Compound No. 45 | 2923, 2850, 1766, 1627, 1596, 1580, 1511, 1486, 1468, 1427, 1363, 1330, 1290, 1238, 1224, 1198, 1154, 1133, 1092, 1000, 982, 933, 903, 884, 819, 752, 727 |
| Example 1-10 | Compound No. 46 | 2925, 2851, 1759, 1627, 1597, 1583, 1509, 1487, 1469, 1365, 1325, 1226, 1207, 1156, 1134, 1092, 1043, 1004, 980, 936, 913, 901, 882, 833, 817, 751, 728, 714 |
| Example 1-11 | Compound No. 47 | 2918, 2849, 1761, 1746, 1629, 1598, 1509, 1487, 1467, 1369, 1321, 1227, 1153, 1133, 1091, 1011, 939, 908, 887, 811, 751, 725 |
| Example 1-12 | Compound No. 48 | 2926, 2856, 1768, 1629, 1599, 1507, 1487, 1459, 1368, 1333, 1204, 1153, 1135, 1094, 1002, 934, 891, 819, 751 |
| Example 1-13 | Compound No. 49(1) | 2930, 1760, 1630, 1599, 1510, 1484, 1326, 1202, 1153, 1133, 1091, 1004, 922, 824, 776, 752, 696 |
| Example 1-14 | Compound No. 49(2) | 2960, 2930, 2866, 1770, 1629, 1599, 1517, 1484, 1460, 1365, 1326, 1200, 1140, 1090, 1008, 931, 898, 864, 823, 804, 778, 753, 734, 697 |
| Example 1-15 | Compound No. 50 | 2918, 2853, 1766, 1600, 1507, 1486, 1334, 1211, 1152, 1094, 1002, 936, 911, 876, 825, 751, 715 |
| Example 1-16 | Compound No. 51 | 2928, 1764, 1750, 1630, 1599, 1505, 1487, 1456, 1365, 1332, 1218, 1204, 1153, 1134, 1092, 999, 957, 895, 879, 827, 751, 695 |
| Example 1-17 | Compound No. 53 | 2961, 2871, 1765, 1630, 1600, 1513, 1483, 1364, 1330, 1204, 1157, 1133, 1092, 1004, 931, 843, 815, 752, 687 |
| Example 1-18 | Compound No. 54 | 2929, 1768, 1602, 1508, 1484, 1329, 1250, 1201, 1155, 1092, 1003, 930, 815, 752, 732 |
| Example 1-19 | Compound No. 55 | 2929, 1764, 1600, 1510, 1484, 1329, 1203, 1132, 1091, 930, 753 |
| Example 1-20 | Compound No. 56 | 2931, 1753, 1607, 1509, 1483, 1328, 1199, 1121, 1091, 1043, 926, 817, 752 |
| Example 1-21 | Compound No. 57 | 2979, 1764, 1509, 1484, 1329, 1274, 1233, 1195, 1119, 1009, 944, 752 |
| Example 1-22 | Compound No. 58 | 2960, 2930, 1764, 1601, 1515, 1484, 1365, 1329, 1198, 1159, 1133, 1092, 1005, 952, 918, 864, 819, 794, 752, 704, 644 |

TABLE 3

| | Oxime Ester Compound | $^1$H-NMR(CDCl$_3$) |
|---|---|---|
| Example 1-1 | Compound No. 1 | 0.85 (t, 3H), 0.92 (t, 3H), 1.20-1.44 (m, 8H), 2.03 (dddddd, 1H), 2.32 (s, 3H), 2.54 (s, 3H), 4.21 (dd, 1H), 4.24 (dd, 1H), 7.42 (d, 1H), 7.46 (d, 1H), 8.06 (dd, 1H), 8.40 (dd, 1H), 8.49 (d, 1H), 9.04 (d, 1H) |
| Example 1-2 | Compound No. 2 | 0.85 (t, 3H), 1.18-1.39 (m, 10H), 1.84-1.91 (m, 2H), 2.32 (s, 3H), 2.53 (s, 3H), 4.33 (t, 2H), 7.41 (d, 1H), 7.45 (d, 1H), 8.04 (dd, 1H), 8.37 (dd, 1H), 8.46 (d, 1H), 8.99 (dd, 1H) |
| Example 1-3 | Compound No. 3 | 1.49 (t, 3H), 2.32 (t, 3H), 2.54 (s, 3H), 4.43 (q, 2H), 7.43 (d, 1H), 7.47 (d, 1H), 8.06 (dd, 1H), 8.39 (dd, 1H), 8.48 (d, 1H), 9.01 (d, 1H) |
| Example 1-4 | Compound No. 7 | 1.06 (t, 3H), 2.32 (t, 3H), 2.55 (s, 3H), 3.83 (t, 2H), 4.54 (t, 2H), 7.39 (d, 2H), 8.06 (dd, 1H), 8.39 (dd, 1H), 8.49 (d, 1H), 9.04 (d, 1H) |
| Example 1-5 | Compound No. 10 | 1.22 (t, 3H), 2.32 (t, 3H), 2.54 (s, 3H), 3.29 (s, 3H), 3.37 (d, 1H), 3.38 (d, 1H), 5.09 (s, 2H), 5.20 (ddq, 1H), 7.39 (d, 1H), 7.42 (d, 1H), 8.06 (dd, 1H), 8.41(d, 1H), 8.50 (d, 1H), 9.05 (d, 1H) |
| Example 1-6 | Compound No. 12 | 1.18 (d, 3H), 1.42 (tt, 2H), 1.69 (tt, 2H), 1.92 (tt, 2H), 2.30 (t, 2H), 2.32 (s, 3H), 2.54 (s, 3H), 3.34 (s, 3H), 3.37 (dd, 1H), 3.39 (dd, 1H), 4.37 (t, 2H), 5.07 (ddq, 2H), 7.44 (d, 1H), 7.46 (d, 1H), 8.06 (dd, 1H), 8.40 (dd, 1H), 8.50 (dd, 1H), 9.04 (dd, 1H) |
| Example 1-7 | Compound No. 20 | 0.86 (t, 3H), 1.21-1.68 (m, 18H), 2.31 (s, 3H), 2.99 (t, 2H), 4.59 (t, 2H), 4.69 (t, 2H), 5.80 (dd, 1H), 5.97 (dd, 1H), 6.27 (dd, 1H), 7.50 (d, 1H), 7.52 (d, 1H), 8.02 (dd, 1H), 8.41 (dd, 1H), 8.47 (d, 1H), 9.05 (d, 1H) |
| Example 1-8 | Compound No. 33 | 1.42 (d, 3H), 1.47 (t, 3H), 2.11 (s, 3H), 2.15 (s, 3H), 3.47 (s, 3H), 3.55 (dd, 1H), 3.67 (dd, 1H), 4.43 (q, 2H), 4.67 (ddq, 1H), 6.88 (dd, 1H), 6.93 (d, 1H), 7.05 (d, 1H), 7.43 (d, 1H), 7.46 (d, 1H), 8.05 (d, 1H), 8.17 (d, 1H), 8.39 (dd, 1H), 8.95 (d, 1H) |
| Example 1-9 | Compound No. 45 | 0.87 (t, 3H), 1.22-1.33 (m, 18H), 1.87 (tt, 2H), 2.31 (s, 3H), 2.54 (s, 3H), 4.35 (t, 2H), 7.43 (d, 1H), 7.46 (d, 1H), 8.06 (dd, 1H), 8.40 (dd, 1H), 8.49 (d, 1H), 9.04 (d, 1H) |
| Example 1-10 | Compound No. 46 | 0.87 (t, 3H), 1.23-1.38 (m, 22H), 1.89 (tt, 2H), 2.32 (s, 3H), 2.54 (s, 3H), 4.36 (t, 2H), 7.44 (d, 1H), 7.47 (d, 1H), 8.06 (dd, 1H), 8.41 (dd, 1H), 8.50 (d, 1H), 9.05 (d, 1H) |
| Example 1-11 | Compound No. 47 | 0.87 (t, 3H), 1.22-1.33 (m, 26H), 1.89 (tt, 2H), 2.31 (s, 3H), 2.54 (s, 3H), 4.36 (t, 2H), 7.44 (d, 1H), 7.47 (d, 1H), 8.06 (dd, 1H), 8.41 (dd, 1H), 8.50 (d, 1H), 9.06 (d, 1H) |
| Example 1-12 | Compound No. 48 | 0.84-0.96 (m, 9H), 1.25-1.69 (m, 18H), 2.05 (dddddd, 1H), 2.32 (s, 3H), 3.00 (t, 2H), 4.24 (d, 2H), 7.43 (d, 1H), 7.47 (d, 1H), 8.02 (dd, 1H), 8.40 (dd, 1H), 8.47 (d, 1H), 9.06 (d, 1H) |
| Example 1-13 | Compound No. 49(1) | 0.85 (t, 3H), 0.92 (t, 3H), 1.22-1.43 (m, 8H), 2.03 (dddddd, 1H), 2.13 (s, 3H), 4.23 (d, 2H), 7.38-7.45 (m, 4H), 7.51-7.55 (m, 3H), 7.97 (dd, 1H), 8.19 (s, 1H), 8.37 (dd, 1H), 8.91 (d, 1H) |
| Example 1-14 | Compound No. 49(2) | 0.88 (t, 3H), 0.98 (t, 3H), 1.24-1.50 (m, 8H), 2.11 (dddddd, 1H), 2.17 (s, 3H), 4.27 (d, 2H), 7.38-7.45 (m, 4H), 7.51-7.55 (m, 3H), 8.13 (d, 1H), 8.41 (dd, 1H), 8.96 (d, 1H) |
| Example 1-15 | Compound No. 50 | 0.85 (t, 3H), 0.86 (t, 3H), 0.93 (t, 3H), 1.16-1.50 (m, 24H), 1.56-1.70 (m, 2H), 2.04 (dddddd, 1H), 2.30 (s, 3H), 2.98 (t, 2H), 4.21 (d, 2H), 7.42 (d, 1H), 7.46 (d, 1H), 8.01 (dd, 1H), 8.40 (dd, 1H), 8.46 (d, 1H), 9.05 (d, 1H) |
| Example 1-16 | Compound No. 51 | 0.84 (t, 3H), 0.91 (t, 3H), 1.16-1.46 (m, 8H), 2.01 (dddddd, 1H), 2.26 (s, 3H), 4.20 (d, 2H), 4.39 (s, 2H), 7.17-7.33 (m, 5H), 7.39 (d, 1H), 7.42 (d, 1H), 8.02 (dd, 1H), 8.38 (dd, 1H), 8.51 (d, 1H), 8.98 (d, 1H) |
| Example 1-17 | Compound No. 53 | (1): 0.87 (t, 3H), 0.92 (t, 3H), 1.27-1.52 (m, 8H), 1.42 (s, 9H), 1.98-2.14 (m, 1H), 2.17 (s, 3H), 4.23 (d, 2H), 7.16-7.58 (m, 6H), 7.95 (dd, 1H), 8.22 (d, 1H), 8.38 (dd, 1H), 8.94 (d, 1H)<br>(2): 0.85 (t, 3H), 0.97 (t, 3H), 1.27-1.52 (m, 8H), 1.34 (s, 9H), 1.98-2.14 (m, 1H), 2.15 (s, 3H), 4.27 (d, 2H), 7.16-<br>(1)/(2) = 52/48 |
| Example 1-18 | Compound No. 54 | (1): 0.87 (t, 3H), 0.97 (t, 3H), 1.22-1.46 (m, 8H), 1.34 (d, 3H), 2.01-2.14 (m, 1H), 2.12 (s, 3H), 3.41 (s, 3H), 3.51 (dd, 1H), 3.59 (dd, 1H), 4.26 (d, 2H), 4.61 (ddq, 1H), 6.92 (ddd, 2H), 7.41 (d, 1H), 7.45 (d, 1H), 7.54 (ddd, 2H), 7.58 (dd, 1H), 8.10 (d, 1H), 8.38 (dd, 1H), 8.97 (d, 1H)<br>(2): 0.85 (t, 3H), 0.92 (t, 3H), 1.22-1.46 (m, 8H), 1.41 (d, 3H), 2.01-2.14 (m, 1H), 2.17 (s, 3H), 3.46 (s, 3H), 3.55 (dd, 1H), 3.66 (dd, 1H), 4.23 (d, 2H), 4.68 (ddq, 1H), 7.04 (ddd, 2H), 7.36 (ddd, 2H), 7.44 (d, 1H), 7.51 (d, 1H), 7.95 (dd, 1H), 8.21 (d, 1H), 8.41 (dd, 1H), 8.95 (d, 1H)<br>(1)/(2) = 53/47 |
| Example 1-19 | Compound No. 55 | 0.85 (t, 3H), 0.92 (t, 3H), 1.19-1.46 (m, 8H), 2.03 (dddddd, 1H), 2.10 (s, 3H), 3.18 (s, 3H), 3.50 (t, 2H), 4.10 (t, 2H), 4.21 (dd, 1H), 4.23 (dd, 1H), 7.09 (dd, 1H), 7.11 (dd, 1H), 7.18 (dd, 1H), 7.40 (d, 1H), 7.42 (d, 1H), 7.50 (ddd, 1H), 8.02 (dd, 1H), 8.19 (d, 1H), 8.37 (dd, 1H), 8.91 (d, 1H) |
| Example 1-20 | Compound No. 56 | 0.86 (t, 3H), 0.93 (t, 3H), 1.16 (t, 3H), 1.21-1.49 (m, 8H), 1.51 (t, 3H), 2.05 (dddddd, 1H), 2.14(s, 3H), 3.99 (q, 2H), 4.15 (q, 2H), 4.23 (dd, 1H), 4.25 (dd, 1H), 6.60 (dd, 1H), 6.61 (d, 1H), 7.10 (d, 1H), 7.41 (d, 1H), 7.43 (d, 1H), 8.06 (dd, 1H), 8.18 (d, 1H), 8.38 (dd, 1H), 8.94 (d, 1H) |
| Example 1-21 | Compound No. 57 | 1.12 (d, 6H), 1.44 (d, 6H), 1.49 (t, 3H), 2.13 (s, 3H), 4.43 (q, 2H), 4.48 (sep, 1H), 4.65 (sep, 1H), 6.56 (dd, 1H), 6.56 (d, 1H), 7.06 (d, 1H), 7.42 (d, 1H), 7.44 (d, 1H), 8.02 (dd, 1H), 8.19 (d, 1H), 8.39 (dd, 1H), 8.94 (d, 1H) |
| Example 1-22 | Compound No. 58 | 0.85 (t, 3H), 0.92 (t, 3H), 1.21-1.46 (m, 8H), 2.03 (dddddd, 1H), 2.10 (s, 3H), 2.20 (s, 3H), 4.23 (d, 2H), 7.05 (ddd, 1H), 7.10 (dd, 1H), 7.14 (dd, 1H), 7.41 (d, 1H), 7.44 (d, 1H), 8.02 (dd, 1H), 8.13 (d, 1H), 8.38 (dd, 1H), 8.93 (d, 1H) |

Example 2

Preparation of Photosensitive Composition No. 1

To 14.0 g of an acrylic copolymer were added 5.90 g of trimethylolpropane triacrylate, 2.70 g of compound No. 1 obtained in Example 1-1, and 79.0 g of ethyl cellosolve, and the mixture was thoroughly stirred to obtain photosensitive composition No. 1.

The acrylic copolymer used above was obtained by dissolving 20 parts by mass of methacrylic acid, 15 parts by mass of hydroxyethyl methacrylate, 10 parts by mass of methyl methacrylate, and 55 parts by mass of butyl methacrylate in 300 parts by mass of ethyl cellosolve, adding thereto 0.75 parts by mass of azobisisobutyronitrile, followed by heating at 70° C. for 5 hours in a nitrogen atmosphere.

Example 3

Preparation of Photosensitive Composition No. 2

Photosensitive composition No. 2 was obtained in the same manner as in Example 2, except for replacing compound No. 1 prepared in Example 1-1 with 2.70 g of compound No. 2 prepared in Example 1-2.

Example 4

Preparation of Photosensitive Composition No. 3

Photosensitive composition No. 3 was obtained in the same manner as in Example 2, except for replacing compound No. 1 prepared in Example 1-1 with 2.70 g of compound No. 3 prepared in Example 1-3.

Example 5

Preparation of Photosensitive Composition No. 4

Photosensitive composition No. 4 was obtained in the same manner as in Example 2, except for replacing compound No. 1 prepared in Example 1-1 with 2.70 g of compound No. 7 prepared in Example 1-4.

Example 6

Preparation of Photosensitive Composition No. 5

Photosensitive composition No. 5 was obtained in the same manner as in Example 2, except for replacing compound No. 1 prepared in Example 1-1 with 2.70 g of compound No. 10 prepared in Example 1-5.

Example 7

Preparation of Photosensitive Composition No. 6

Photosensitive composition No. 6 was obtained in the same manner as in Example 2, except for replacing compound No. 1 prepared in Example 1-1 with 2.70 g of compound No. 12 prepared in Example 1-6.

Example 8

Preparation of Photosensitive Composition No. 7

Dipentaerythritol pentaacrylate (15.0 g) and 3.74 g of 1,4-butanediol diglycidyl ether were mixed, and 3.30 g of compound No. 1 obtained in Example 1 and 78 g of ethyl cellosolve were added thereto, followed by thoroughly stirring to make photosensitive composition No. 7.

Example 9

Preparation of Photosensitive Composition No. 8 as Alkali-Developable Photosensitive Resin Composition Step 1-Preparation of Alkali Developable Resin Composition No. 8

In a reactor were put 17.0 g of 1,1-bis(4'-epoxypropyloxyphenyl)-1-(1"-biphenyl)-1-cyclohexylmethane, 4.43 g of acrylic acid, 0.06 g of 2,6-di-tert-butyl-p-cresol, 0.11 g of tetrabutylammonium acetate, and 14.3 g of propylene glycol-1-monomethyl ether-2-acetate and stirred at 120° C. for 16 hours. The reaction system was cooled room temperature, and 7.18 g of propylene glycol-1-monomethyl ether-2-acetate, 4.82 g of succinic anhydride, and 0.25 g of tetrabutylammonium acetate, were added thereto, followed by stirring at 100° C. for 5 hours. To the mixture were further added 5.08 g of 1,1-bis(4'-epoxypropyloxyphenyl)-1-(1"-biphenyl)-1-cyclohexylmethane and 2.18 g of propylene glycol-1-monomethyl ether-2-acetate, and the mixture was stirred at 120° C. for 12 hours, 80° C. for 2 hours, and 40° C. for 2 hours. Finally, 13.1 g of propylene glycol-1-monomethyl ether-2-acetate was added to give alkali developable resin composition No. 8 in the form of a propylene glycol-1-monomethyl ether-2-acetate solution (Mw=4200; Mn=2100; acid value (solid basis): 55 mg-KOH/g).

Step 2-Preparation of Photosensitive Composition No. 8

Alkali developable resin composition No. 8 obtained in step 1 above (2.68 g), 0.73 g of trimethylolpropane triacrylate, 7.91 g of propylene glycol-1-monomethyl ether-2-acetate, and 5.18 g of cyclohexanone were mixed. Compound No. 1 obtained in Example 1 (1.58 g) was added thereto, followed by stirring well to give photosensitive composition No. 8 as an alkali developable photosensitive resin composition.

Example 10

Preparation of Photosensitive Composition No. 9 as Alkali-Developable Photosensitive Resin Composition Step 1-Preparation of Alkali Developable Resin Composition No. 9

In a reactor were put 184 g of a bisphenol fluorene epoxy resin (epoxy equivalent: 231), 58.0 g of acrylic acid, 0.26 g of 2,6-di-tert-butyl-p-cresol, 0.11 g of tetrabutylammonium acetate, and 23.0 g of propylene glycol-1-monomethyl ether-2-acetate and stirred at 120° C. for 16 hours. After cooling to room temperature, 35.0 g of propylene glycol-1-monomethyl ether-2-acetate, 59.0 g of biphthalic anhydride, and 0.24 g of tetra-n-butylammonium bromide were added to the reaction system, followed by stirring at 120° C. for 4 hours. To the mixture were further added 20 g of tetrahydrophthalic anhydride, and the mixture was stirred at 120° C. for 4 hours, 100° C. for 3 hours, 80° C. for 4 hours, 60° C. for 6 hours, and 40° C. for 11 hours. Finally, 90.0 g of propylene glycol-1-monomethyl ether-2-acetate was added to give alkali developable resin composition No. 9 in the form of a propylene glycol-1-monomethyl ether-2-acetate solution (Mw=5000; Mn=2100; acid value (solid basis): 92.7 mg-KOH/g).

Step 2-Preparation of Photosensitive Composition No. 9

Alkali developable resin composition No. 9 obtained in step 1 above (2.68 g), 0.73 g of trimethylolpropane triacrylate, 7.91 g of propylene glycol-1-monomethyl ether-2-acetate, and 5.18 g of cyclohexanone were mixed. Compound No. 1 obtained in Example 1 (1.58 g) was added thereto to give photosensitive composition No. 9 as an alkali developable photosensitive resin composition.

Example 11

Preparation of Photosensitive Composition No. 10 as Colored Alkali-Developable Photosensitive Resin Composition Photosensitive composition No. 10, which was a colored alkali-developable photosensitive resin composition, was prepared in the same manner as in Example 9, except for further adding 2.00 g of pigment blue 15.

Example 12

Preparation of Photosensitive Composition No. 11 as Colored Alkali-Developable Photosensitive Resin Composition Photosensitive composition No. 11, which was a colored alkali-developable photosensitive resin composition, was prepared in the same manner as in Example 10, except for further adding 3.00 g of carbon black.

Example 13

Preparation of Photosensitive Composition No. 12

Photosensitive composition No. 12 was prepared in the same manner as in Example 2, except for further adding 4.52 g of titanium oxide.

Comparative Example 1

Preparation of Photosensitive Composition No. 13

Photosensitive resin composition No. 13 for comparison was prepared in the same manner as in Example 2, except for replacing compound No. 1 obtained in Example 1-1 with 2.70 g of comparative compound 1 shown below.

[Formula 23]

Comparative compound 1

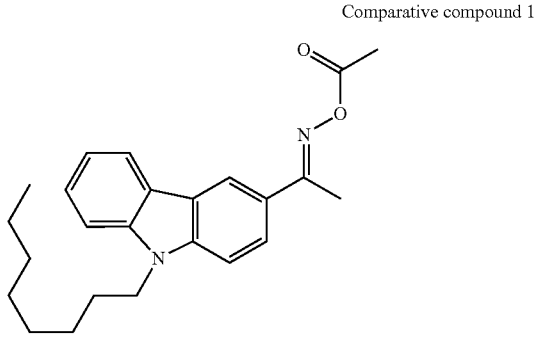

Comparative Example 2

Preparation of Photosensitive Composition No. 14 as Alkali Developable Photosensitive Resin Composition Photosensitive resin composition No. 14 as a comparative alkali developable photosensitive resin composition was prepared in the same manner as in Example 9, except for replacing 1.58 g of compound No. 1 obtained in Example 1-1 with 1.58 g of comparative compound 1.

Photosensitive composition No. 1 and photosensitive composition No. 13 for comparison were tested for hardness as follows. The results obtained are shown in Table 4.

Photosensitive composition No. 8, which was an alkali developable photosensitive resin composition, and photosensitive resin composition No. 14, which was an alkali developable photosensitive resin composition for comparison, were evaluated for sensitivity as follows. The results are shown in Table 5.

Hardness Test

The photosensitive composition was applied to a 50 μm thick polyethylene terephthalate film with a #3 bar coater and irradiated with light of a high pressure mercury lamp (80 W/cm) using a light irradiator equipped with a belt conveyor. The distance between the lamp and the belt conveyor was 10 cm. The linear speed of the belt conveyor was 8 cm/min. After the thus cured coating layer was left to stand at room temperature for 24 hours, the hardness was measured using a pencil hardness tester under a load of 1 kg.

Sensitivity

The alkali developable photosensitive resin composition was applied to an aluminum plate with a #3 bar coater to a thickness of about 1 μm, prebaked at 60° C. for 15 minutes, and exposed to light of an ultra-high pressure mercury lamp using a spectrophotometer CT-25CP form JASCO Corp. The exposed coating layer was dipped in a 2.5 mass % solution of sodium carbonate at 25° C., followed by thoroughly washing with water. The spectral sensitivity at 365 nm and 405 nm was evaluated in terms of the minimum energy of light at 365 nm and 405 nm necessary for the coating layer to sufficiently cure to remain on the aluminum plate.

TABLE 4

| Photosensitive Composition | Pencil Hardness |
|---|---|
| No. 1 (Example 2) | 3H |
| No. 13 (Comparative Example 1) | 1H |

TABLE 5

| | Sensitivity (mJ/cm$^2$) | |
|---|---|---|
| Photosensitive Composition | 365 nm | 405 nm |
| No. 8 (Example 9) | 5.9 | 2.4 |
| No. 14 (Comp. Example 2) | 18.6 | 762 |

Photosensitive composition No. 1 of Example 2 gained high hardness on curing, whereas photosensitive composition No. 13 of Comparative Example 1 failed to provide sufficient hardness. Alkali developable photosensitive resin composition No. 8 of Example 9 exhibited high sensitivity to light of long wavelengths, i.e., 365 nm and 405 nm, whereas alkali developable photosensitive resin composition No. 14 of Comparative Example 2 required an increased amount of energy for exposure at 365 nm and 405 nm on account of low sensitivity to these wavelengths of light.

Example 14

Preparation of Photosensitive Composition No. 15 as Colored Alkali Developable Photosensitive Resin Composition Alkali developable resin composition No. 8 obtained in step 1 of Example 9 (11.5 g), 0.3 g of a mixture of dipentaerythritol pentaacrylate and dipentaerythritol hexaacrylate, 6.6 g of carbon black, 30.0 g of propylene glycol-1-monomethyl ether-2-acetate, and 30.0 g of cyclohexanone were mixed. Compound No. 54 obtained in Example 1-17 (1.0 g) was added thereto, followed by stirring well to give photosensitive composition No. 15 as a colored alkali developable photosensitive resin composition.

Comparative Example 3

Preparation of Photosensitive Composition No. 16 as Colored Alkali Developable Photosensitive Resin Composition Photosensitive composition No. 16 as a comparative colored alkali-developable photosensitive resin composition was prepared in the same manner as in Example 14, except for replacing compound No. 54 obtained in Example 1-17 with 1.0 g of comparative compound 1.

Photosensitive composition No. 15 and comparative photosensitive composition No. 16 were evaluated as follows. The results obtained are shown in Table 6.

The colored alkali-developable photosensitive resin composition was applied to a glass substrate by spin coating at 900 rpm for 10 seconds and prebaked at 70° C. for 20 minutes. The coating film was exposed to light from a high pressure mercury lamp through a mask of prescribed pattern, dipped in a 2.5 mass % aqueous solution of sodium carbonate at 25° C. for 40 seconds, followed by thoroughly washing with water. After drying, the thus developed coating film was baked at 230° C. for 1 hour to fix the pattern. The resulting pattern was evaluated as follows.

Sensitivity

A photosensitive composition that succeeded in patterning with an exposure energy of 60 mJ/cm$^2$ was graded A. A photosensitive composition that failed to form a pattern until the exposure energy was raised to 100 mJ/cm$^2$ or 150 mJ/cm$^2$ was graded B or C, respectively.

Resolution

A photosensitive composition that succeeded in forming a satisfactory pattern of a line width of 8 μm or less was graded A. A photosensitive composition that succeeded in forming a good pattern with a line width of from 10 to 30 μm was graded B. A photosensitive composition that succeeded to form a good pattern with a line width of 30 μm or more was graded C.

Adhesion

The pattern formed by the development was inspected for peeling. A pattern suffering from no peeling was rated "good", while a pattern suffering from peeling in part was rated "poor".

TABLE 6

| Photosensitive Composition | Sensitivity | Resolution | Adhesion |
|---|---|---|---|
| No. 15 (Example 14) | A | A | good |
| No. 16 (Comp. Example 3) | C | C | poor |

The photosensitive composition 15 of Example 14, which was a colored, alkali-developable photosensitive resin composition, exhibited high sensitivity and high resolution and provided a cured film with high adhesion to the substrate and no peeling. In contrast, photosensitive composition 16 of Comparative Example 3, which was a colored, alkali-developable photosensitive resin composition, had low sensitivity, low resolution, and poor adhesion to the substrate.

INDUSTRIAL APPLICABILITY

The oxime ester compound of the invention exhibits high photosensitivity, particularly to long wavelengths of light at 365 nm (i-rays) and 405 nm (h-rays), and is therefore useful as a photopolymerization initiator.

The invention claimed is:

1. An oxime ester compound of the following formula:

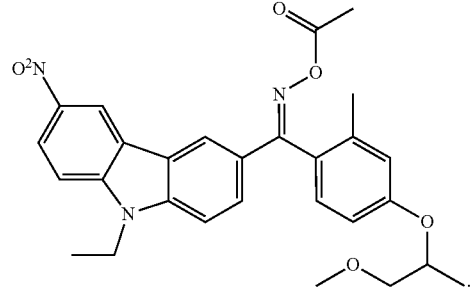 [SMILES: CCn1c2ccc(/C(=N/OC(C)=O)c3ccc(OC(C)COC)cc3C)cc2c2cc([N+](=O)[O-])ccc21]

2. An oxime ester compound of the following formula:

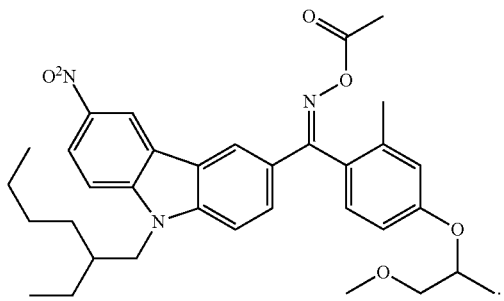 [SMILES: CCCCC(CC)Cn1c2ccc(/C(=N/OC(C)=O)c3ccc(OC(C)COC)cc3C)cc2c2cc([N+](=O)[O-])ccc21]

* * * * *